US012702690B2

(12) United States Patent
Cao et al.

(10) Patent No.: US 12,702,690 B2
(45) Date of Patent: Aug. 11, 2026

(54) CANNABINOID COMPOSITIONS AND DOSAGE FORMS FOR INTRANASAL OR INHALATIONAL DELIVERY

(71) Applicants: RHODES TECHNOLOGIES, Coventry, RI (US); UNIVERSITY OF SOUTH FLORIDA, Tampa, FL (US)

(72) Inventors: Chuanhai Cao, Tampa, FL (US); Ping Chang, Waterford, CT (US)

(73) Assignees: RHODES TECHNOLOGIES, Coventry, RI (US); UNIVERSITY OF SOUTH FLORIDA, Tampa, FL (US)

(*) Notice: Subject to any disclaimer, the term of this patent is extended or adjusted under 35 U.S.C. 154(b) by 475 days.

(21) Appl. No.: 17/999,640

(22) PCT Filed: May 26, 2021

(86) PCT No.: PCT/US2021/034156

§ 371 (c)(1),
(2) Date: Nov. 22, 2022

(87) PCT Pub. No.: WO2021/242808

PCT Pub. Date: Dec. 2, 2021

(65) Prior Publication Data

US 2023/0233635 A1 Jul. 27, 2023

Related U.S. Application Data

(60) Provisional application No. 63/030,083, filed on May 26, 2020.

(51) Int. Cl.

| | |
|---|---|
| ***A61K 36/185*** | (2006.01) |
| ***A61K 9/00*** | (2006.01) |
| ***A61K 9/48*** | (2006.01) |
| ***A61K 9/51*** | (2006.01) |
| ***A61K 31/00*** | (2006.01) |
| ***A61K 47/34*** | (2017.01) |

(52) U.S. Cl.
CPC ........ *A61K 36/3482* (2024.05); *A61K 9/0043* (2013.01); *A61K 9/4833* (2013.01); *A61K 9/5153* (2013.01); *A61K 31/658* (2023.05); *A61K 47/34* (2013.01)

(58) Field of Classification Search
None
See application file for complete search history.

(56) References Cited

U.S. PATENT DOCUMENTS

| | | | |
|---|---|---|---|
| 2007/0060639 | A1 | 3/2007 | Wermeling |
| 2011/0171144 | A1 | 7/2011 | Wang et al. |
| 2011/0311630 | A1 | 12/2011 | Krueger et al. |
| 2013/0266617 | A1 | 10/2013 | Mirosevich et al. |
| 2018/0042860 | A1 | 2/2018 | Banderas et al. |
| 2019/0031834 | A1 | 1/2019 | Blanco et al. |
| 2023/0000770 | A1 | 1/2023 | Tan et al. |

FOREIGN PATENT DOCUMENTS

| | | | |
|---|---|---|---|
| EP | 3257503 | 12/2017 | |
| JP | 2001-526221 | 12/2001 | |
| JP | 2011-522859 | 8/2011 | |
| WO | 199932107 | 7/1999 | |
| WO | 2019113685 | 6/2019 | |
| WO | WO-2019113685 A1 * | 6/2019 | ............. A61K 9/107 |
| WO | 2020/094908 | 5/2020 | |
| WO | 2021/109823 | 6/2021 | |

OTHER PUBLICATIONS

Office Action issued Nov. 12, 2024 in connection with European Application No. 21813263.7.
European Search Report issued Mar. 26, 2024 in connection with Application No. 21813263.7.
International Search Report and Written Opinion mailed Sep. 8, 2021 in connection with PCT/US21/34156.
Office Action issued May 8, 2025 in connection with Japanese Application No. 2022-572535.
Zhang et al., "Preparation, characterization and application of pyrene-loaded methoxy poly(ethylene glycol)-poly(lactic acid) copolymer nanoparticles," Colloid Polym Sci, 2004, vol. 282, pp. 1323-1328.
Suzuki et al., "Transport Mechanism in the Nose-to-Brain Delivery and Role of Nanosystems," Oleo Science, Feb. 2020, vol. 2, pp. 61-69.
Office Action issued Mar. 17, 2025 in connection with Taiwan Patent Application No. 110119036.

* cited by examiner

*Primary Examiner* — Melissa S Mercier
(74) *Attorney, Agent, or Firm* — Troutman Pepper Locke LLP

(57) ABSTRACT

The present invention provides pharmaceutical compositions and methods for use and manufacture thereof. The pharmaceutical compositions comprise a therapeutically effective amount of a cannabinoid or a pharmaceutically acceptable salt or solvate thereof and an amphiphilic copolymer comprising at least one hydrophilic component and at least one hydrophobic component. The cannabinoid is encapsulated in the amphiphilic copolymer, and the composition is suitable for intranasal or inhalation delivery.

5 Claims, 39 Drawing Sheets

CANNABINOID COMPOSITIONS AND DOSAGE FORMS FOR INTRANASAL OR INHALATIONAL DELIVERY

CROSS REFERENCE TO RELATED APPLICATION

This application is a 371 National Stage Application of International Application No. PCT/US21/34156, filed May 26, 2021, which claims the benefit of and priority to U.S. Provisional Patent Application No. 63/030,083 filed on May 26, 2020. The entire contents of the applications are incorporated herein by reference in their entirety.

FIELD OF THE INVENTION

The present invention relates to compositions and dosage forms for intranasal or inhalational delivery of cannabinoids. The invention also relates to methods for use and manufacture of the dosage forms and compositions. More specifically, the invention relates to compositions and dosage forms comprising a cannabinoid encapsulated by copolymer to form micelles.

BACKGROUND

Cannabinoids are a class of diverse chemical compounds that act on cannabinoid receptors (CB1 or CB2) in cells that alter neurotransmitter release in the brain. Ligands for these receptor proteins include the endocannabinoids, produced naturally in the body by animals, the phytocannabinoids, found in *Cannabis sativa* and some other plants, and synthetic cannabinoids, manufactured artificially. The most notable cannabinoid is the phytocannabinoid tetrahydrocannabinol ($\Delta^9$-THC), the primary psychoactive compound in *Cannabis sativa*. Cannabidiol (CBD) is another major constituent of the plant and does not bind CB1 or CB2 receptors.

Alzheimer's disease is a progressive neurological disorder where brain cells waste away (degenerate) and die. Alzheimer's disease is the most common cause of dementia—a continuous decline in thinking, behavioral and social skills that disrupts a person's ability to function independently. There is no treatment that cures Alzheimer's disease or alters the disease process in the brain. In advanced stages of the disease, complications from severe loss of brain function—such as dehydration, malnutrition or infection—result in death. Plaques and tangles are believed to be the primary causes of nerve damage in Alzheimer's patients. Plaques are deposits of β-amyloid protein that build up in spaces between nerve cells and tangles are twisted fibers of tau protein that build up within nerve cells.

Targeting the endogenous cannabinoid system has emerged as a potential therapeutic approach to treat Alzheimer (Aso and Ferrer, "Cannabinoids for treatment of Alzheimer's disease: moving toward the clinic," *Front Pharmacol.,* 5:37 (2014); Cao, et al., "The Potential Therapeutic Effects of THC on Alzheimer's Disease," *Journal of Alzheimer's disease* 42:973 (2014)). This system (also called the endocannabinoid system) is composed by a number of cannabinoid receptors, including the well-characterized $CB_1$ and $CB_2$ receptors, with their endogenous ligands and the enzymes related to the synthesis and degradation of these endocannabinoid compounds (id.). Several findings indicate that the activation of both $CB_1$ and $CB_2$ receptors by natural or synthetic agonists, at non-psychoactive doses, can have beneficial effects in Alzheimer experimental models by reducing harmful β-amyloid peptide action and tau phosphorylation, as well as by promoting the brain's intrinsic repair mechanisms (Gemma Navarro et al., "*Receptor-heteromer mediated regulation of endocannabinoid signaling in activated microglia: Role of CB1 and CB2 receptors and relevance for Alzheimer's disease and levodopa-induced dyskinesia*"; Bele'n G. Rami'rez, et al., "*Prevention of Alzheimer's Disease Pathology by Cannabinoids: Neuroprotection Mediated by Blockade of Microglial Activation*). Thus, studies have demonstrated that cannabinoids remove plaque-forming Alzeheimer's proteins (e.g, β-amyloid peptide) from brain cells and thereby reduce cellular inflammation and high rates of neuron death caused by Alzheimer's proteins (Bele' et al, supra. and Currais, et al., "Amyloid proteotoxicity initiates an inflammatory response blocked by cannabinoids," *npj Aging and Mechanisms of Disease*, doi: 10.1038/npjamd.2016.12 (2016)).

Dronabinol, or (−)-trans-$\Delta^9$-tetrahydrocannabinol ($\Delta^9$-THC), is a synthetically produced $\Delta^9$-THC. Dronabinol is used as an appetite stimulant, an anti-emetic and an analgesic. It has the following structural formula:

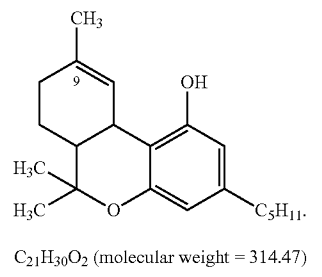

$C_{21}H_{30}O_2$ (molecular weight = 314.47)

Dronabinol is a clear to amber resinous oil that is sticky at room temperature and hardens upon refrigeration. It is insoluble in water, but can be formulated in oil, e.g., sesame oil.

Dronabinol is commercially available under the trade name Marinol®, which is indicated for 1) anorexia associated with weight loss in patients with AIDS and 2) nausea and vomiting associated with cancer chemotherapy in patients who have failed conventional antiemetic treatments. It is provided as a solution in soft gelatin capsules for oral administration, in 2.5 mg, 5 mg, or 10 mg dosages. The formulation includes sesame oil, gelatin, glycerin (glycerol), methylparaben, propylparaben, and titanium dioxide. This formulation is highly unstable at room temperature and requires refrigeration for storage (2-8° C.) or cool conditions (8-15° C.). It should be packaged in a dark, well-closed container and stored in a cool environment between 8° C. and 15° C. (46° F. and 59° F.). See, Marinol® package label, Physicians Desk Reference®, ed. 2003. The bioavailability of dronabinol in this formulation is relatively low, due to first-pass metabolism in the liver, which reduces the concentration of drug that is available for circulation in the bloodstream.

These disadvantages are pronounced for the administration of dronabinol to treat Alzheimer's disease, because the active cannabinoid must cross the blood-brain barrier in suitable amounts, without excessive metabolism, in order to reach the brain and activate its cannabinoid receptors in effective, non-psychoactive doses. Anti-inflammatory and self-repair benefits associated with cannabinoid therapy for Alzheimer's disease also implicate mechanisms in the brain. There is a need for cannabinoid compositions and dosage forms that effectively target the brain, are storage stable, and resist rapid conversion to disadvantageous, e.g. psychoactive, metabolites.

At the present time, nabilone, dronabinol (e.g. Marinol®), nabilone (e.g. Cesamet®) and cannabidiol (e.g. Epidolex, for epilepsy) are the only commercially available approved cannabinoid drugs in the United States. In Europe and Canada, Sativex®, a sublingual spray containing dronabinol and cannabidiol in a ratio of 52:48, is also available for the treatment of multiple sclerosis spasticity. Sativex®, manufactured by GW Pharmaceuticals, is described in U.S. Pat. No. 8,512,767. Like Marinol®, Sativex® must also be refrigerated to maintain chemical stability. Similar to Marinol®, limitations of Sativex® include poor storage stability and pharmacokinetics.

Cannabinoid drug composition stability and dosage accuracy and uniformity remain technical challenges, in view of the low stability, high viscosity, and low water solubility of cannabinoids. Particularly challenging is the manufacture of stable, water-soluble cannabinoid formulations and dosage forms for intranasal administration.

Thus, there exists an unmet need for improved water-soluble compositions and dosage forms comprising a cannabinoid for intranasal delivery.

SUMMARY OF THE INVENTION

Various non-limiting aspects and embodiments of the invention are described below.

The invention provides a pharmaceutical composition comprising a therapeutically effective amount of a cannabinoid, or a pharmaceutically acceptable salt or solvate thereof, in combination with an amphiphilic copolymer comprising at least one hydrophilic component and at least one hydrophobic component. The cannabinoid is encapsulated in the amphiphilic copolymer. The composition is suitable for delivery by intranasal administration or inhalation. In certain embodiments, the hydrophilic component is polyethylene glycol (PEG), and the hydrophobic component is selected from polycaprolactone (PCL), polylactic acid (PLA), and poly lactide co-glycolide (PLGA). The ratio of hydrophilic to hydrophobic components in certain copolymer embodiments ranges from about 1:1 to about 1:5 (by number average molecular weight). In one embodiment, the hydrophobic component is PLGA.

In certain embodiments comprising PEG and PLGA components, the molecular weight (Mn) of PEG is about 2000 to about 5000 and the molecular weight (Mn) of PLGA is about 4500 to about 9000. In certain embodiments, these PEG-PLGA polymers have the general formula

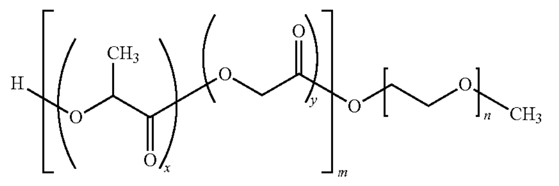

In this formula, m represents the number of repeating units of PLGA and n represents the number of repeating units of PEG (in moles). Likewise, x and y represent the number of repeating units of each PLGA component (in moles). Any suitable values for x, y, m, and are within the scope of the invention. In certain embodiments, each of x and y can range from 1 to 3 and each of m and n can range from 1 to 5. In one suitable PEG-PLGA embodiment, the PEG component has a molecular weight (Mn) of 2000 and the PLGA component has a molecular weight (Mn) of 4500. The ratio of PEG to PLGA for this copolymer is 2000:4500=1:2.25 (by number average molecular weight). In another suitable PEG-PLGA embodiment, the PEG component has a molecular weight (Mn) of 5000 and the PLGA component has a molecular weight (Mn) of 7000. The ratio of PEG to PLGA for this copolymer is 5000:7000=1:1.4 (by number average molecular weight). The cannabinoid preferably is Δ9-THC (dronabinol) or cannabinodiol (CBD).

Compositions of the invention provide a cannabinoid in effective amounts that are suitable for treating a neurological condition, such as Alzheimer's disease, Parkinson's disease, neuropathic pain, spasticity, spinal-cord-injury-induced pain, migraines, multiple sclerosis, Tourette's Syndrome, or post-traumatic stress disease (PTSD). In certain embodiments, an effective amount of the composition is administered to a subject in order treat one of these conditions, for example Alzheimer's disease. The route of administration is intranasal or by inhalation. Thus, the invention also provides a method for treating a neurological disease, including pain, by administering the composition, comprising the encapsulating copolymer and an effective amount of cannabinoid, intranasally or by inhalation, to a subject in need thereof, including a human patient.

In certain embodiments a suitable daily dose for administration to humans is about 0.5 to about 7.5 mg, which may be administered once-daily, in divided doses, preferably twice-daily. In certain embodiments a suitable dose for humans is 2.5 mg administered in one or more doses throughout the day, for example, once-daily, twice daily, or three or more times per day. In certain embodiments the total daily dose is from about 2.5 to about 30 mg. For example the daily dose may be about 2.5 mg, 5.0 mg, 7.5 mg, 10 mg, 20 mg, 25 mg, or 30 mg. In certain embodiments the total daily dose may be from about 10% to about 30% of each of these daily doses. In certain embodiments the total daily dose may be from about 30% to about 50% of each of these daily doses. In certain embodiments, the total daily dose may be from about 50% to about 70% of each of these daily doses. In certain embodiments, a delivery device, such as an intranasal spray or metered dose inhaler may dispense a unit dose of about 2.5 mg of cannabinoid. In certain embodiments, the unit dose may be less than about 2.5 mg, e.g. about 0.5 to less than about 2.5 mg, such as unit doses of 0.2, 0.3, 0.5, 1.0, and 2.0 mg. The composition may comprise one or more cannabinoids, such as a combination of Δ9-THC and CBD, which may be provided in equal or unequal ratios by weight. In embodiments comprising more than one cannabinoid, the unit dose and daily dose of each cannabinoid may be provided separately or together. In certain embodiments, the combined unit and/or daily doses of two or more cannabinoids may fall within the ranges and amounts provided herein. In certain embodiments, the combined unit and/or daily doses of two or more cannabinoids may be proportional to a range or amount provided herein.

The invention advantageously provides an improved storage-stable cannabinoid composition that effectively targets the brain while bypassing undesirable first-pass metabolism. In the body, primarily the liver, the cannabinoid Δ9-THC is hydrolyzed to the psychoactive compound 11-hydroxy Δ9-tetra hydrocannabinol (11-OH-THC), also called OH-THC. Further oxidation generates the inactive 11-nor-9-carboxy-Δ9-tetrahydrocannbinol, also called THC-COOH. The invention advantageously reduces the amount of OH-THC that reaches the brain. Improved solubility, particularly for intranasal or inhaled delivery, provides a more consistent targeted dose of cannabinoid.

These and other aspects of the present invention will become apparent to those skilled in the art after a reading of the following detailed description of the invention, including the appended claims.

BRIEF DESCRIPTION OF THE DRAWINGS

In the figures as presented below, when applicable, bars represent mean±SEM (standard error of the mean); OFC=olfactory cortex; CTX=frontal cortex; HPC=hippocampus; Naked=naked $\Delta^9$-THC formulation ($\Delta^9$-THC oil); Nano=nano-emulsion formulation (a water and oil nano-emulsion of $\Delta^9$-THC); Liquid=a water-based $\Delta^9$-THC formulation; Oil=an oil-based $\Delta^9$-THC formulation; Poly=$\Delta^9$-THC encapsulated by polymeric micelles.

FIG. 2A provides a bar graph showing total drug in blood after 15 min. FIG. 2B provides a bar graph showing total drug in the brain after 15 min. FIG. 2C provides a bar graph showing total drug distribution in the brain after 15 min.

FIG. 3A provides a bar graph showing conversion of $\Delta^9$-THC into its metabolites in whole blood after 15 minutes. FIG. 3B provides a bar graph showing conversion of $\Delta^9$-THC into its metabolites in the brain after 15 minutes.

FIG. 5A provides a bar graph showing total drug in blood after 30 min. FIG. 5B provides a bar graph showing total drug in the brain after 30 min. FIG. 5C provides a bar graph showing total drug distribution in the brain after 30 min.

FIG. 6A provides a bar graph showing conversion of $\Delta^9$-THC to its metabolites in blood after 30 min. FIG. 6B provides a bar graph showing conversion of $\Delta^9$-THC to its metabolites in brain after 30 min.

FIG. 8A provides a bar graph showing total drug in blood after 45 min. FIG. 8B provides a bar graph showing total drug in the brain after 45 min.

FIG. 9A provides a bar graph showing $\Delta^9$-THC conversion in blood after 45 min. FIG. 9B provides a bar graph showing $\Delta^9$-THC conversion in the brain after 45 min.

FIG. 11A provides a bar graph showing total drug in blood. FIG. 11B provides a bar graph showing total drug in the brain. FIG. 11C provides a bar graph showing drug distribution in the brain.

FIG. 12A provides a bar graph showing $\Delta^9$-THC conversion in blood. FIG. 12B provides a bar graph showing $\Delta^9$-THC conversion in the brain.

FIGS. 14A-14D provide scatter plots of $\Delta^9$-THC, THC-OH, THC-COOH, and total drug over time, respectively.

FIGS. 15A-15C provide scatter plots of $\Delta^9$-THC, THC-OH, and THC-COOH in blood over time, respectively. FIGS. 15D-15F provide scatter plots of $\Delta^9$-THC, THC-OH, and THC-COOH in the brain over time, respectively.

FIG. 16A provides a bar graph showing total drug in blood. FIG. 16B provides a bar graph showing total drug ($\Delta^9$-THC and its metabolites) in the brain. FIG. 16C provides a bar graph showing drug distribution in the brain.

FIG. 17A provides a bar graph showing $\Delta^9$-THC conversion in blood. FIG. 17B provides a bar graph showing $\Delta^9$-THC conversion in the brain.

DETAILED DESCRIPTION

Figure 1:
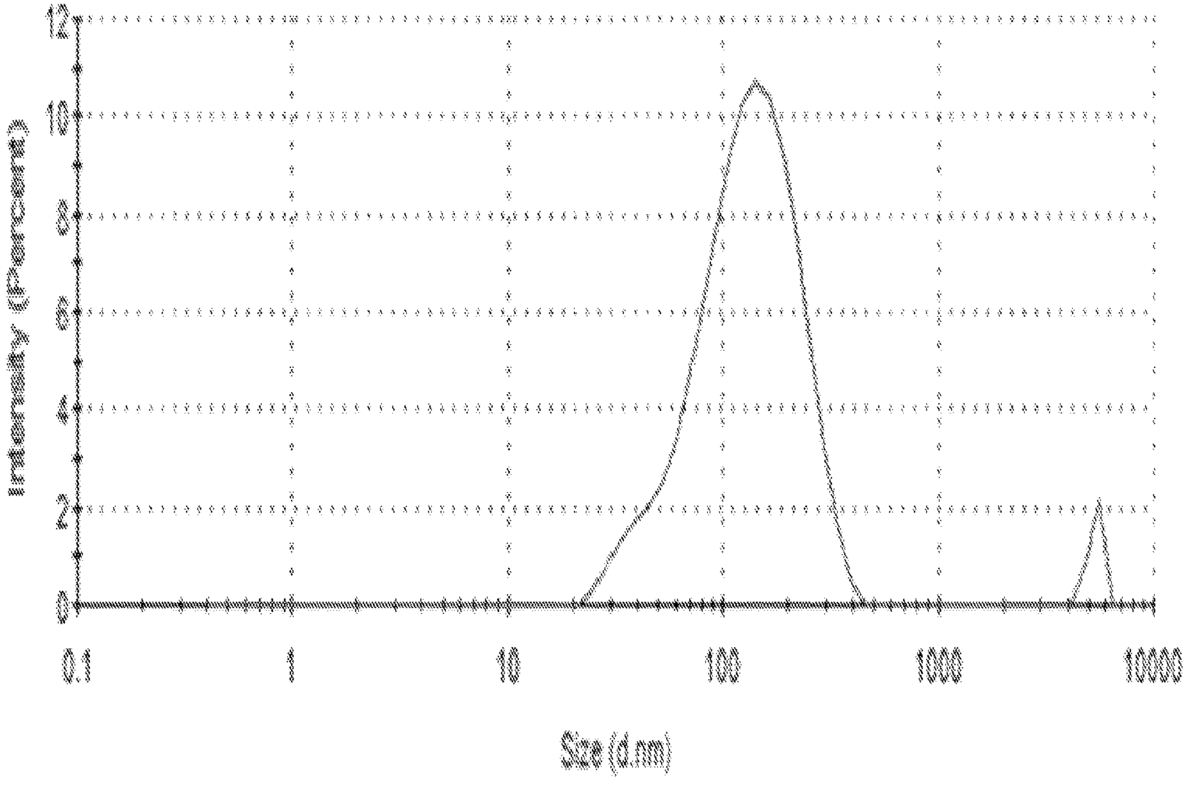
FIG. 1 provides a plot of dynamic light scattering (DLS) data. The plot shows particle distribution by intensity for polymeric micelles (PM) prepared according to embodiments of the present invention. d.nm=diameter in nanometers.

Detailed embodiments of the present invention are disclosed herein; however, it is to be understood that the disclosed embodiments are merely illustrative of the invention that may be embodied in various forms. In addition, each of the examples given in connection with the various embodiments of the invention is intended to be illustrative, and not restrictive. Therefore, specific structural and functional details disclosed herein are not to be interpreted as limiting, but merely as a representative basis for teaching one skilled in the art to variously employ the present invention.

The pharmaceutical composition of the invention may be provided in any suitable dosage form, including for example a powder, a liquid, or a liquid reconstituted from a powder, which may or may not be a lyophilized powder. In various embodiments, the device suitable for intranasal delivery includes a spray pump, metered-dose pump or inhaler, pressurized spray or inhaler, nebulizer, atomizer, aerosol device, or any device suitable for intranasal or nasal inhalation delivery of a liquid or powder composition.

The pharmaceutical compositions and dosage forms of the invention can be used for the treatment, the slowing of progression, or the alleviation of symptoms of conditions including Alzheimer's disease, Parkinson's disease, neuropathic pain, spasticity, spinal-cord-injury-induced pain, migraines, multiple sclerosis, Tourette syndrome, post-traumatic stress disease (PTSD) and various combinations thereof. In various embodiments, the compositions and dosage forms according to the invention may be used particularly for the treatment, or the slowing of progression of Alzheimer's disease. Certain embodiments provide that the compositions and dosage forms of the invention are useful for symptomatic relief of conditions including spasticity (muscle stiffness/spasm) and/or neuropathic pain due to multiple sclerosis (MS), as well as analgesic treatment for cancer patients who experience pain while on opioid therapy.

In certain embodiments, the compositions and dosage forms according to the invention can also be used to treat conditions including chemotherapy-induced emesis, nausea, and/or vomiting in patients with cancer, to treat HIV/AIDS-related anorexia, and/or as an appetite stimulant.

The compositions and dosage forms according to the invention may also be used to treat migraines.

As described in detail below, the present inventors have discovered that water soluble compositions or formulations of cannabinoids may be prepared by encapsulation of the cannabinoids by polymeric micelles comprising specific amphiphilic copolymers and using a particular method. Surprisingly, the polymeric micelle encapsulated cannabinoids result in advantageous metabolic and drug-targeting characteristics relative to alternative drug forms when administered to a mammal. Further, the polymeric micelle encapsulated cannabinoids surprisingly demonstrate clinical and metabolic characteristics closely resembling those of naked cannabinoids (e.g., naked $\Delta^9$-THC), albeit without psychoactive effects (e.g. a "high").

General Definitions

Unless defined otherwise, all technical and scientific terms used herein have the same meaning as commonly understood by one of ordinary skill in the art to which this invention belongs.

As used in this specification and the appended claims, the singular forms "a", "an", and "the" include plural references unless the context clearly dictates otherwise. Thus, for example, a reference to "a method" includes one or more methods, and/or steps of the type described herein and/or which will become apparent to those persons skilled in the art upon reading this disclosure.

In connection with a measured number, quantity amount or range, the terms "about" and "approximately" refer to normal measurement variations, according to a level of care that is appropriate for the objective of the measurement and is consistent with the precision of the measuring equipment or method. For example, in certain embodiments, the term "about" includes ±10%, such that "about 10" would include from 9 to 11. Ranges and ratios can be expressed herein as from "about" or "approximately" one particular value to "about" or "approximately" another particular value. For example, unless otherwise stated, a range of "about 1-5" is synonymous with a range of "about 1 to about 5."

The term "composition," as used herein, are includes the disclosure of both a composition and a composition administered in a method as described herein. Furthermore, in some embodiments, the composition of the present invention is or comprises a "formulation," which may alternatively be referred to as a dosage form.

As used herein the term "effective" applied to dose or amount, including a therapeutic amount, refers to that quantity of a compound or pharmaceutical composition that is sufficient to result in a desired activity upon administration to a subject in need thereof. Note that when a combination of active ingredients is administered, the effective amount of the combination may or may not include amounts of each ingredient that would have been effective if administered individually. The exact amount required will vary from subject to subject, depending on the species, age, and general condition of the subject, the severity of the condition being treated, the particular drug or drugs employed, the mode of administration, and the like.

The term "polymeric micelle," as used herein, refers to nanocarriers that are formed according to methods of the present disclosure by spontaneous arrangement of amphiphilic component copolymers in aqueous solutions. Amphiphilic block copolymers are copolymers comprising hydrophilic blocks and hydrophobic blocks. The nanostructures have a hydrophobic core-hydrophilic shell architecture that facilitates the loading of cannabinoids or other hydrophobic drugs into the core. Polymeric micelles are self-assembled core-shell nanostructures formed in an aqueous solution comprising amphiphilic block copolymers. A cannabinoid become encapsulated by a polymeric micelle when the cannabinoid is disposed within the core of a polymeric micelle. Formation of micelles in aqueous solution occurs when the concentration of the block copolymer increases above a critical aggregation concentration or critical micelle concentration leading to formation of a vesicular or core-shell micellular structure. Polymeric micelles advantageously are easy to manufacture.

The term "intranasal administration," "intranasal delivery," "nasal delivery," or "intranasal," as used herein, refers to administration of a drug to the nasal cavity such that the drug contacts and becomes initially disposed within mucosa or upon epithelial surfaces within the nasal canal of a subject. When a drug is administered intranasally the drug enters a subject through epithelia disposed within the nasal cavity (e.g., respiratory epithelium or olfactory epithelium). In various embodiments, "intranasal administration" results in at least 100%, 99%, 98%, 97%, 96%, 95%, 94%, 93%, 92%, 91%, 90%, 85%, 80%, 75%, 70%, 65%, 60%, 55%, 50%, 45%, 40%, 35%, 30%, 25%, or 20% by weight of a cannabinoid administered to a subject entering the body of the subject via the olfactory epithelium or via epithelia lining the nasal cavity (i.e., absorbed into the body through or by surfaces and cellular processes associated with the olfactory epithelium or surfaces of the nasal cavity, respectively). In various embodiments, intranasal administration is achieved by inhalation. In various embodiments, a subject does not inhale during intranasal administration.

The phrase "intranasal administration by inhalation" or "inhalation," as used herein, unless indicated as otherwise, refers to a patient taking air into the lungs during intranasal administration of a drug to create a flow of air into the nasal cavity as a means of facilitating efficient delivery of the drug to the nasal cavity and not to the lungs. Synonyms of "intranasal administration by inhalation" or "inhalation," as used herein, include "snorting," "snuffing," and "sniffing." "Inhalation" and "intranasal administration by inhalation" are methods of intranasal administration and, therefore, fall within a genus of administration methods encompassed by the term "intranasal administration."

The terms "level" and "concentration," as used herein, are used interchangeably.

The term "solvate," as used herein, is used to refer to an aggregate that consists of a solute ion or molecule and one or more solvent molecules. The term "solute," as used herein, refers to a substance that may be dissolved by a solvent or that can be the minor component of a solution comprising the solvent, and the term "solvent," as used herein, refers to a substance capable of dissolving other substances (i.e., the solute) or that can be the major component of a solution. The term "hydrate," as used herein, refers to a solvate wherein the solvent is water. Solvates and hydrates of a drug substance are crystal modifications of a drug substance comprising the drug and solvent molecules. Solvates are formed when a compound (e.g., a drug) crystallizes with solvent entrapped within the resulting crystal structure. Crystals comprising no solvent are referred to as "anhydrates" rather than "solvates." Solvates contain either stoichiometric or non-stoichiometric amounts of a solvent, and in some embodiments are formed during the process of crystallization with pharmaceutically acceptable solvents such as water, ethanol, and the like. Alcoholates are formed when the solvent is alcohol. In general, the solvated forms are considered equivalent to the unsolvated forms for the purposes of the compositions, formulations and methods provided herein.

The terms "treat," "treating" or "treatment," and other grammatical equivalents as used herein, include alleviating, inhibiting or reducing symptoms, reducing or inhibiting severity of, reducing incidence of, reducing or inhibiting recurrence of, delaying onset of, delaying recurrence of, abating or ameliorating a disease or condition symptoms, ameliorating the underlying causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms further include achieving a therapeutic benefit. By therapeutic benefit is meant eradication or amelioration of the underlying disorder being treated, and/or the eradication or amelioration of one or more of the physiological symptoms associated with the underlying disorder such that an improvement is observed in the patient.

The terms "subject", "patient", or "individual" are used interchangeably herein and refer to mammals and non-mammals, e.g., suffering from a disorder described herein. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "effective amount", "pharmacologically effective amount", "physiologically effective amount" or "therapeutically effective amount," as used herein, refer to a sufficient amount of a therapeutic agent or a compound being administered which will relieve to some extent one or more of the symptoms of the disease or condition being treated. The result is reduction and/or alleviation of the signs, symptoms, or causes of a disease, or any other desired alteration of a biological system. For example, an "effective amount" for therapeutic uses is the amount of the composition that includes a drug described herein required to provide a desired level of drug (e.g., $\Delta^9$-THC) in the bloodstream or at the site of action (e.g., the brain) of a subject to be treated and thereby produce a clinically significant decrease in disease symptoms. The precise amount will depend upon numerous factors, e.g., the specific therapeutic agent, the activity of the therapeutic agent, the delivery device employed, the physical characteristics of the therapeutic agent, intended use by the subject (i.e., the number of doses administered per day), subject considerations, and the like, and can readily be determined by one skilled in the art. In some embodiments, an appropriate "effective" amount in any individual case is determined using techniques, such as a dose escalation study. In certain instances, an "effective amount" for therapeutic uses is the amount of the composition comprising an agent as set forth herein required to provide a clinically significant decrease in a disease. An appropriate "effective" amount in any individual case is determined using any suitable technique, such as a dose escalation study.

The terms "administer," "administering", "administration," "deliver," and the like, as used herein, refer to the methods that may be used to enable delivery of agents or compositions to the desired site of biological action. These methods include, but are not limited to, oral routes and nasal routes. Administration techniques that are optionally employed with the agents and methods described herein are found in sources e.g., Goodman and Gilman, The Pharmacological Basis of Therapeutics, current ed.; Pergamon; and Remington's, Pharmaceutical Sciences (current edition), Mack Publishing Co., Easton, Pa. In certain embodiments, the agents and compositions described herein are administered intranasally.

The term "acceptable" with respect to a formulation, composition or ingredient, as used herein, means having no persistent detrimental effect on the general health of the subject being treated.

Polymers consist of repeat units (monomers) chemically bonded into long chains of unequal length. As used herein, the "molecular weight" of a polymer, also called its molecular mass, is an average of the distribution of chain lengths and molecular weights, which may also be referred to by polymer suppliers as its published molecular weight or "grade." The number average molecular mass ("Mn") is the ordinary arithmetic mean or average of the molecular masses of the individual polymer components; i.e. the total weight of polymer divided by the total number of molecules. The weight average molecular weight of a polymer ("Mw") is its average molar mass, which depends on the fraction of the total weight represented by each of the polymer components.

Unless otherwise stated, references herein to the molecular weight of a specific polymer refers to a number average molecular weight ("Mn"), or to a published molecular weight or grade for that polymer (if available), however the published molecular weight is determined.

The phrase "pharmaceutically acceptable", as used in connection with compositions of the invention, refers to molecular entities and other ingredients of such compositions that are physiologically tolerable and do not typically produce untoward reactions when administered to a mammal (e.g., a human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

The term "pharmaceutical composition," as used herein, refers to a mixture of a therapeutic agent (e.g., $\Delta^9$-THC) described herein with one or more other components. In preferred embodiments of the invention such other components include a polymeric micelle, a carrier and/or excipients such fluidizers, lubricants, preservatives, surfactants, anti-static agents, anti-microbial agents, preservatives and the like. The pharmaceutical composition can facilitate administration of a therapeutic agent to an organism, for example by intranasal administration.

The terms "pharmaceutically acceptable salt" or "salt" includes, but is not limited to: (1) acid addition salts, formed by reacting the freebase form of a therapeutic agent with a pharmaceutically acceptable inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; (2) salts formed when an acidic proton present in the parent therapeutic agent is replaced by a metal ion, e.g., an alkali metal ion (e.g. lithium, sodium, potassium), an alkaline earth ion (e.g. magnesium, or calcium), or an aluminum ion. In some cases, therapeutic agents may coordinate with an organic base, such as, but not limited to, ethanolamine, diethanolamine, triethanolamine, tromethamine, N-methylglucamine, dicyclohexylamine, tris(hydroxymethyl)methylamine. In other cases, therapeutic agents form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

The compositions of the invention may comprise at least one propellant as a delivery vehicle. As used herein, the term "propellant" includes any volatile short chain hydrocarbon, hydrofluoroalkane, or chlorofluorocarbon approved by the Food and Drug Administration for use in pressurized containers to create movement of a fluid from the dispenser.

The term "biodegradable," as used herein, refers to a compound that may be broken down and metabolized by a subject.

Cannabinoids

The term "cannabinoid" or "cannabinoid derivative" relates to any cannabinoid isolated from the *Cannabis sativa* plant or any synthetically created compound that interacts with a cannabinoid receptor or is a cannabinoid mimetic and/or derivative, including as non-limiting examples tetrahydrocannabinol (THC), cannabidiol (CBD), cannabinol (CBN), and dodeca-E,4E,8Z,10E/Z-tetraenoic-acid-isobutylamides, cannabigerol (CBG), cannabichromene, cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethylether (CBGM), and nabilone. Further examples of cannabinoids and cannabinoid derivatives include cannabigerolic acid, $\Delta^9$-tetrahydrocannabinolic acid (COOH-THC), cannabidiolic acid, cannabichromenenic acid, cannabigerovarinic acid, tetrahydrocanabivarinic acid, cannabidivarinic acid, cannabichromevarinic acid, OH-THC, cannabigerol, $\Delta^9$-tetrahydrocannabinol, cannabidiol, cannabichromene, cannabigerivarin, tetrahydrocannabivarin, cannabidivarin, cannabinodiol, cannabicyclol, cannabielsoin, cannabitriol, cannabichromevarin, or various combinations thereof. In various embodiments, the cannabinoid is selected from $\Delta^9$-THC (dronabinol), nabilone, and cannabinodiol (CBD).

In some embodiments, the active pharmaceutical ingredient in the composition is tetrahydrocannabinol (THC) or a pharmaceutically acceptable salt thereof. In various embodiments, the active pharmaceutical ingredient in the composition is nabilone. THC exists in many isomeric forms, including (+)-trans-$\Delta^8$-tetrahydrocannabinol, (+trans-$\Delta^8$-tetrahydrocannabinol, (+)-trans-$\Delta^9$-tetrahydrocannabinol, and (−)-trans-$\Delta^9$-tetrahydrocannabinol (or dronabinol; trade name Marinol®). Structures of THC positional and stereoisomers include the following:

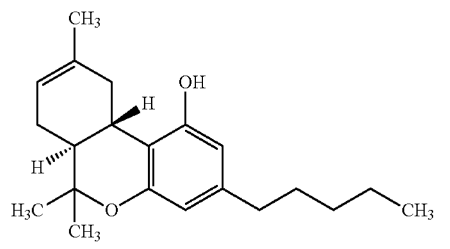

(+)-$\Delta^8$-THC

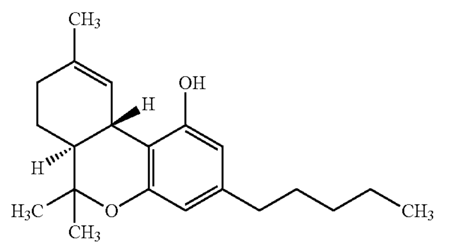

(+)-$\Delta^9$-THC

-continued

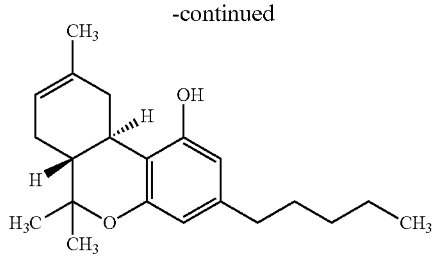

(-)-$\Delta^8$-THC

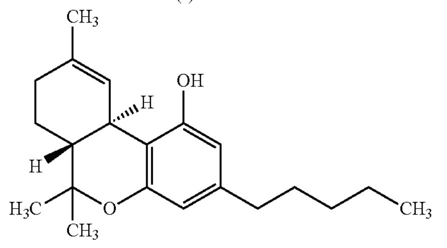

(-)-$\Delta^9$-THC (−)-trans-$\Delta^9$-THC (dronabinol) is the major natural constituent of *Cannabis sativa*. The $\Delta^9$-THC and $\Delta^8$-THC isomers have similar pharmacological profiles, although $\Delta^9$-THC has a higher potency than $\Delta^8$-THC isomers, and their solubilities are essentially identical. Although $\Delta^8$-THC is more stable, does not undergo oxidation to cannabinol and has a much longer shelf life than $\Delta^9$-THC, it is less potent in most pharmacological tests (see, e.g., Ophthalmic Res. (1992) 24: 142-149). Thus, there is a need for stabilized formulations comprising $\Delta^9$-THC (dronabinol) and other active cannabinoid compounds and derivatives.

OH-THC is the primary active metabolite of $\Delta^9$-THC and COOH-THC is the primary inactive metabolite of $\Delta^9$-THC (Sharma, et al., "Chemistry, Metabolism, and Toxicology of Cannabis: Clinical Implications," *Iran J. Psychiatry,* 7:149-156 (2012). Hydroxylation of $\Delta^9$-THC generates the psychoactive compound OH-THC. Following ingestion of $\Delta^9$-THC, systemic absorption typically peaks within 1-2 hours (id.).

Pharmaceutical Compositions

In one aspect, the invention provides for a pharmaceutical composition comprising a cannabinoid, or a pharmaceutically acceptable salt or solvate thereof, and an amphiphilic copolymer. The composition comprises a therapeutically effective amount of the cannabinoid or the pharmaceutically acceptable salt or solvate thereof. The amphiphilic copolymer comprises at least one hydrophilic component or block(s) and at least one hydrophobic component or block(s). The cannabinoid is encapsulated in the amphiphilic copolymer and the resulting composition is shelf-stable, particularly at room temperature, and is suitable for intranasal, nasal, or inhalation delivery. Encapsulation by polymeric micelles has been demonstrated previously as increasing shelf stability of otherwise unstable drugs and resulting in a sustained release effect during drug administration (Hu, et al. *International Journal of Pharmaceutics,* 450:331-337 (2013), the disclosure of which is incorporated herein by reference to demonstrate the stabilizing and sustained release effect of polymeric micelles on a drug encapsulated thereby).

Active Cannabinoid Ingredient

In various embodiments, the drug or active ingredient as contained in the pharmaceutical composition or a dosage form of the invention is any cannabinoid, as provided above, and various mixtures thereof. In various embodiments, the cannabinoid is $\Delta^9$-THC (dronabinol), pharmaceutically acceptable salts or solvates thereof, or various combinations thereof. In various embodiments, the administered pharmaceutical compositions of the invention do not include a metabolite of $\Delta^9$-THC as an active ingredient. In various embodiments, the drug or active ingredient is nabilone, pharmaceutically acceptable salts or solvates thereof, or various combinations thereof. Another suitable active ingredient is cannabidiol (CBD). In some embodiments Δ9-THC and CBD are used in combination with each other.

Polymeric Micelles

In various embodiments, the amphiphilic copolymer forms polymeric micelles encapsulating the cannabinoid. In various embodiments, the polymeric micelles have an average diameter of from about 10 to about 500 nm, from about 50 to about 250 nm, from about 50 to about 200 nm, from about 10 nm to about 50 nm, from 10 nm to about 100 nm, from 10 nm to about 75 nm, or from about 100 to about 150 nm. In various embodiments, the polymeric micelles have an average diameter of about or of at least about 10 nm, 20 nm, 25 nm, 30 nm, 40 nm, 50 nm, 55 nm, 60 nm, 65 nm, 70 nm, 75 nm, 80 nm, 85 nm, 90 nm, 95 nm, 100 nm, 110 nm, 115 nm, 120 nm, 125 nm, 130 nm, 135 nm, 140 nm, 145 nm, 150 nm, 155 nm, 160 nm, 165 nm, 170 nm, 175 nm, 180 nm, 185 nm, 190 nm, 195 nm, 200 nm, 225 nm, 250 nm, 275 nm, 300 nm, 325 nm, 350 nm, 375 nm, or 400 nm. In various embodiments, the polymeric micelles have an average diameter of no more than about 20 nm, 25 nm, 30 nm, 40 nm, 50 nm, 55 nm, 60 nm, 65 nm, 70 nm, 75 nm, 80 nm, 85 nm, 90 nm, 95 nm, 100 nm, 110 nm, 115 nm, 120 nm, 125 nm, 130 nm, 135 nm, 140 nm, 145 nm, 150 nm, 155 nm, 160 nm, 165 nm, 170 nm, 175 nm, 180 nm, 185 nm, 190 nm, 195 nm, 200 nm, 225 nm, 250 nm, 275 nm, 300 nm, 325 nm, 350 nm, 375 nm, 400 nm, or 450 nm.

In various embodiments, the polymeric micelle is coupled to a targeting ligand (e.g., a lectin or an antibody). As a non-limiting example, a lectin can be covalently bound to an outer surface of the polymeric micelle to facilitate entrapment of the polymeric micelle within a mucosal layer within the nasal cavity. Entrapment of the polymeric micelle within the mucosal layer within the nasal cavity can increase a residence time of the polymeric micelle within the nasal cavity and thereby improve efficiency of release of drug within the nasal cavity. As a further non-limiting example, an antibody can be covalently bound to the outer surface of the polymeric micelle to facilitate targeting of the polymeric micelle to the mucosal layer within the nasal cavity or to a surface of a cell disposed within the nasal cavity. In various embodiments, the antibody may bind to a surface protein of an epithelial cell disposed within the nasal cavity or the antibody may bind to a polysaccharide or peptide component of the mucosal layer within the nasal cavity.

Amphiphilic Copolymers

The polymeric micelles encapsulating the cannabinoid are formed by amphiphilic copolymers. In various embodiments, the amphiphilic copolymer comprises a hydrophobic block component and a hydrophilic block component. In various embodiments, the amphiphilic copolymer is a diblock copolymer (A-B or B-A type, where A represents a hydrophilic block and B represents a hydrophobic block), a tri-block copolymer (A-B-A type or A-B-C type, where C represents a hydrophobic or a hydrophilic block), a graft copolymer, or a charged copolymer. In some embodiments, the amphiphilic copolymer is a di-block copolymer comprising a single hydrophobic block and a single hydrophilic block. In various embodiments, the amphiphilic copolymer is biodegradable.

The molecular weight of a polymer or copolymer, or polymeric component may be determined by any suitable method, or as specified by any manufacturer or supplier thereof (e.g., the polymer "grade"). Unless indicated otherwise, the molecular weight of a polymer or copolymer, or polymeric component refers to number-average molecular weight ("Mn"). In various embodiments, the amphiphilic copolymer comprises a hydrophilic block. In some embodiments the hydrophilic block comprises or consists of poly (ethylene glycol) (PEG), or poly(ethylene oxide) (PEO), or various mixtures thereof. In various embodiments, the hydrophilic block has a weight-average or number-average molecular weight in Daltons, preferably a number average molecular weight, of about or of at least about 1,000 Da, 1,250 Da, 1,500 Da, 1,750 Da, 2,000 Da, 2,250 Da, 2,500 Da, 2,750 Da, 3,000 Da, 3,250 Da, 3,500 Da, 4,000 Da, 4,250 Da, 4,500 Da, 4,750 Da, 5,000 Da, 5,250 Da, 5,500 Da, 5,750 Da, or 6,000 Da. In various embodiments, the hydrophilic block has a molecular weight of not more than about 1,500 Da, 1,750 Da, 2,000 Da, 2,250 Da, 2,500 Da, 2,750 Da, 3,000 Da, 3,250 Da, 3,500 Da, 4,000 Da, 4,250 Da, 4,500 Da, 4,750 Da, 5,000 Da, 5,250 Da, 5,500 Da, 5,750 Da, 6,000 Da, or 6,500 Da. In various embodiments, the hydrophilic block has a weight-average or number-average molecular weight, preferably a number average molecular weight, of from about 500 Da to about 7,000 Da, from about 750 Da to about 6,500 Da, from about 900 Da to about 6,000 Da, from about 1,500 to about 6,000 Da, from about 1,750 to about 6,000 Da, or from about 2,000 to about 5,000 Da.

In various embodiments, the amphiphilic copolymer comprises a hydrophobic block. In various embodiments, the hydrophobic block comprises or consists of a poly(L-amino acid), a biodegradable poly(ester), phospholipids/long chain fatty acids, polypropylene oxide, or various combinations thereof. In various embodiments, the hydrophobic block comprises or consists of poly(lactic-co-glycolic acid) (PLGA). Non-limiting examples of a biodegradable poly (ester) include poly(glycolic acid), polylactic acid (PLA) (e.g., poly(D,L-lactic acid) or poly(D-lactic acid)), copolymers of lactide/glycolide, and poly(ε-caprolactone)/polycaprolactone (PCL). In various embodiments, the hydrophobic block is selected to be compatible with the cannabinoid so as not to interfere with or detrimentally chemically interact with the cannabinoid and to effectively facilitate encapsulation of the cannabinoid by the polymeric micelle.

In various embodiments, the hydrophobic block has a number average molecular weight in Daltons of about or of at least about 3,000 Da, 3,250 Da, 3,500 Da, 4,000 Da, 4,250 Da, 4,500 Da, 4,750 Da, 5,000 Da, 5,250 Da, 5,500 Da, 5,750 Da, 6,000 Da, 6,250 Da, 6,500 Da, 6,750 Da, 7,000 Da, 7,250 Da, 7,500 Da, 7,750 Da, 8,000 Da, 8,250 Da, 8,500 Da, 8,750 Da, or 9,000 Da. In various embodiments, the hydrophilic block has a number average molecular weight of not more than about 3,250 Da, 3,500 Da, 4,000 Da, 4,250 Da, 4,500 Da, 4,750 Da, 5,000 Da, 5,250 Da, 5,500 Da, 5,750 Da, 6,000 Da, 6,250 Da, 6,500 Da, 6,750 Da, 7,000 Da, 7,250 Da, 7,500 Da, 7,750 Da, 8,000 Da, 8,250 Da, 8,500 Da, 8,750 Da, or 9,000 Da. In various embodiments, the hydrophilic block has a molecular weight (Mn) of from about 1,000 Da to about 9,000 Da, from about 1,500 Da to about 8,000 Da, from about 3,000 Da to about 8,000 Da, from about 4,000 Da to about 8,000 Da, from about 4,000 to about 7,500 Da, from about 4,000 to about 7,500 Da, from about 4,500 Da to about 9,000 Da, or from about 4,000 to about 10,000 Da.

In various embodiments, the amphiphilic copolymer comprises the hydrophilic block and the hydrophobic block in a ratio, by number average molecular weight, of from about 1:10 to about 10:1, from about 1:100 to about 100:1, from about 1:5 to about 5:1, from about 1:20 to about 20:1, from about 30:1 to about 1:30, from about 1:2 to about 2:1, from about 3:1 to about 3:1, from about 4:1 to about 1:4, from about 6:1 to about 1:6, from about 1:7 to about 7:1, from about 8:1 to about 1:8, or from about 9:1 to about 1:9. In various embodiments, the amphiphilic copolymer comprises the hydrophilic block and the hydrophobic block in a ratio, by number average molecular weight, of about 1:1, 1:2, 1:3, 1:4, 1:5, 1:6, 1:7, 1:8, 1:9, or 1:10. Without being bound by any theory, the hydrophobic polymer preferably predominates over the hydrophilic polymer in order to more effectively encapsulate the cannabinoid within suitable micelles, while the hydrophilic polymer confers water-solubility to the composition.

In various embodiments the hydrophilic component of the amphiphilic copolymer is polyethylene glycol (PEG) and the hydrophobic component is selected from polycaprolactone, polylactic acid, and poly lactide co-glycolide (PLGA). In some embodiments, the composition is prepared and administered as a liquid or powder and is lyophilized. In other embodiments, powders and lyophilized formulations are reconstituted before administration.

It has been appreciated in the art that drug delivery via the olfactory mucosa, or mucous membrane, is a viable route for delivering certain drugs. Formulations for intranasal delivery of cannabinoids may offer multiple advantages over oral dosage forms, such as enabling the drug to be absorbed directly through the mucosal lining which has a very rich vascular blood supply, resulting in faster onset, and bypassing the blood-brain barrier (Ganger and Schindowski, "Tailoring Formulations for Intranasal Nose-to-Brain Delivery: A Review on Architecture, Physico-Chemical Characteristics and Mucociliary Clearance of the Nasal Olfactory Mucosa," *Pharmaceutics,* 10:116 (2018)). Further, intranasal drug delivery avoids issues associated with first pass metabolism. As such, intranasal delivery can be advantageous when rapid onset of action, better efficacy, and bypass of the blood-brain barrier is desired. A drug for intranasal delivery may result in better compliance than orally ingested forms, such as tablets or capsules, by patients who have difficulty swallowing or suffer from emesis and anorexia.

In some embodiments of the invention, the pharmaceutical composition is suitable for intranasal or nasal delivery, or is delivered by inhalation.

In various embodiments, the device suitable for intranasal delivery includes a spray pump, metered-dose pump or inhaler, pressurized spray or inhaler, nebulizer, atomizer, aerosol device, or any device suitable for intranasal or nasal inhalation delivery of a liquid or powder composition. In a preferred embodiment, the pharmaceutical composition is a liquid, which may or may not be reconstituted from a powder, and the powder may or may not be lyophilized. In a further preferred embodiment the liquid is delivered by a device comprising a spray pump.

Excipients

In various embodiments, excipients suitable for intranasal delivery can be added to the composition or formulation of the present invention. Frequently excipients serve to improve features of the composition, e.g., by providing more efficient and reproducible delivery of the therapeutic agent, improving the handling characteristics of powders (e.g., flowability and consistency), the stability of the agent, and/or facilitating manufacturing and filling of unit dosage forms. In certain embodiments, excipient materials function to further improve the physical and chemical stability of a cannabinoid, aid in adhesion or binding a formulation into the nasal mucosal layer and enhance uptake of the cannabinoid into the mucosal cells, thus increasing efficacy of the cannabinoid. Excipients can further serve to minimize residual moisture content and/or hinder moisture uptake, minimize particle aggregation, modify particle surface properties (i.e., rugosity), increase the ease of delivery, improve targeting of particles to the sinuses. In some embodiments, an excipient also serves as a bulking agent when it is desired to reduce the concentration of cannabinoid in the formulation. Furthermore, an excipient can server as a masking agent for objectionable smells and/or tastes.

Useful excipients that can be added to the compositions and formulations of the invention include, but are not limited to, mucoadhesive agents (e.g., cross-linked polyacrylic acids, carboxymethylene, carboxymethyl cellulose, alginate, chitosan, polyacrylic acid, hyaluronic acid, carbopol, hydroxypropyl cellulose, methylcellulose, polyelectrolytes and their derivatives), fluidizers, lubricants (e.g., magnesium stearate), adhesion agents, surfactants, acidifying agents, alkalizing agents, agents to adjust pH, antimicrobial preservatives (e.g., lipophilic preservatives, chlorobutol, hydroxybenzoates, methylhydroxybenzoates, propylhydroxybenzoates, chlorobutol, phenylmercuric acetate, thiomersal, benzalkonium chloride, menthol, eucalyptolxylomethazoline, oxymethazoline, and various combinations thereof), adsorption enhancers (e.g., cyclodextins, bile salts, laureth-9 sulfate, fusidate derivatives, fatty acids, hydrophilic polymers, surfactants, β-cyclodextrins, and the like) antioxidants, anti-static agents, buffering or pH adjustment agents, chelating agents, humectants, gel-forming agents, or wetting agents. Excipients also include coloring agents, coating agents, sweetening, flavoring and perfuming and other masking agents.

In certain embodiments, the compositions and formulations of this invention include a formulation with an individual excipient or with multiple excipients in any suitable combination. In some embodiments, a fluidizer is added to the composition to improve the flowability of the composition. Typically, fluidizers help to prevent compositions from aggregating or clumping and allow for improved powder handling. Use of fluidizers may increase capsule filling efficiency and consistency along with increasing dose administration consistency and efficiency of the nasal administration devices. Examples of fluidizers include tribasic calcium phosphate, magnesium stearate, or disclosed in U.S. Pat. No. 5,098,907, anhydrous silicic acid. Fluidizing agents can be used alone or in combination. In some embodiments, tribasic calcium phosphate is used.

Agents to adjust pH include, for example, dibasic sodium phosphate, citric acid, and sodium citrate. Examples of pharmaceutically acceptable antioxidants include water soluble antioxidants such as ascorbic acid, cysteine hydrochloride, sodium bisulfate, sodium metabisulfite, sodium sulfite and the like, while examples of oil-soluble antioxidants such include ascorbyl palmitate, butylated hydroxyanisole (BHA), butylated hydroxytoluene (BHT), lecithin, propyl gallate, alpha-tocopherol and the like. Examples of preservatives include, for example, benzalkonium chloride.

Suitable antistatic agents may be selected from, for example, sorbitan fatty acid esters, polyoxyethylene sorbitan fatty acid esters, dioctyl sodium sulphosuccinate, and fatty amine salts of alkylarylsulphonic acids. Suitable anti-static agents are also disclosed in International Application WO 94/04133.

In some embodiments, adhesion agents are bioadhesion and/or mucoadhesion promoting agents. In some embodiments, the adhesion agents are carrier particles, while in other embodiments, the adhesion agents coat the carrier particles or the therapeutic agent. Alternatively, the adhesion agent can be added to the formulation in its free state unbound to the carrier or drug. Bioadhesion and/or mucoadhesion agents increase the adherence of a therapeutic agent or agents to the nasal mucosa. Generally, the bioadhesion and/or mucoadhesion promoting agents swell and expand when placed in contact with water.

Typically, bioadhesion and/or mucoadhesion promoting agent is a polymeric substance that can be hydrated leading to swelling of the polymer. Generally, the faster the swelling of the polymer, the faster is the initiation of bioadhesion and/or mucoadhesion. Exemplary bioadhesion and/or mucoadhesion promoting agents are disclosed in U.S. Patent Application Serial No. 20060216352, the disclosure of which is incorporated herein by reference to provide examples of bioadhesion and/or mucoadhesion promoting agents. Examples of bio/mucoadhesion promoting agents include polymers such as celluloses (e.g. micro-crystalline cellulose), cellulose derivatives, starch, starch derivatives, cross-linked polymers based on e.g. starch, cellulose, polyvinylpyrrolidone, and various combinations thereof. Furthermore, inorganic salts can be used as bio/mucoadhesion promoting agents; e.g., as calcium phosphate, dicalcium phosphate hydrate, dicalcium phosphate dihydrate, tricalcium phosphate, calcium carbonate, barium sulfate, and various combinations thereof. Further specific non-limiting examples of bio/mucoadhesion promoting agents include cellulose derivatives such as hydroxypropylmethyl cellulose (HPMC), hydroxyethyl cellulose (HEC), hydroxypropyl cellulose (HPC), methyl cellulose, ethyl hydroxyethyl cellulose, carboxymethyl cellulose and sodium carboxymethyl cellulose (NaCMC); starch derivatives such as moderately cross-linked starch; acrylic polymers such as carbomer and its derivatives (Polycarbophyl, Carbopol®, etc.); polyethylene oxide (PEO); chitosan (poly-(D-glucosamine)); natural polymers such as gelatin, sodium alginate, pectin; scleroglucan; xanthan gum; guar gum; poly co-(methylvinyl ether/maleic anhydride); and crosscaramellose; and various combinations thereof.

Examples of pH adjustment agents include magnesium hydroxide and aluminum hydroxide. Examples of chelating agents include citric acid, ethylenediamine tetraacetic acid (EDTA), sorbitol, tartaric acid, and phosphoric acid. Useful surfactants include bile acid surfactants as disclosed in U.S. Pat. No. 6,815,424 or phosphatidylcholines, such as dipalmitoylphosphatidylcholine, diphosphatidyl glycerol, hexadecanol, fatty alcohols such as polyethylene glycol, polyoxyethylene-9-lauryl ether, a surface active fatty acid, such as palmitic acid or oleic acid, or other surfactants as disclosed in U.S. Pat. No. 5,855,913.

In some embodiments of the invention, a water-absorbing and gel-forming material is added to the composition to improve drug absorption. Typically, this gel-forming material is used as a carrier, either alone or in combination with a water-absorbing, but non-gel-forming substance. Exemplary, gel-forming material include for example cellulose derivatives such as hydroxypropyl cellulose, hydroxypropyl methyl cellulose, methyl cellulose, hydroxy ethyl cellulose, and carboxymethyl cellulose sodium. Further disclosure of water-absorbing and gel-forming material and their use is found in U.S. Pat. No. 6,835,389.

Representative examples of wetting agents include, for example, gelatin, casein, lecithin (phosphatides), gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., TWEEN™), polyethylene glycols, polyoxyethylene stearates, colloidal silicon dioxide, phosphates, sodium dodecyl sulfate, carboxymethylcellulose calcium, carboxymethylcellulose sodium, methylcellulose, hydroxyethyl cellulose, hydroxy propylcellulose, hydroxypropylmethylcellulose phthalate, noncrystalline cellulose, magnesium aluminum silicate, triethanolamine, polyvinyl alcohol, and polyvinylpyrrolidone (PVP).

Useful sweetening agents include, for example, D-sorbitol, glycyrrhiza, saccharin, and stevia.

Generally, pharmaceutical excipients, if present, range in amounts from about 0.01% to about 95% by weight. More typically, excipients range from about 0.5 to about 80%, about 1.0% to about 50%, or about 5% to about 30% by weight of the composition.

Therapeutic agents, carriers, excipients, and other components may require grinding, milling, spray drying, or some other processing step before use. Frequently, the required processing converts the therapeutic agents into particles with a desired median size and/or a defined particle size distribution ranges. In some embodiments, the native or processed therapeutic agents, carriers, excipients, and other components are suitable for intranasal use, as is. In other embodiments, these ingredients require further processing, such as sieving, to achieve the desired or necessary particle size distributions.

Methods of Manufacture

In one aspect, the present invention provides for a method for manufacture of a polymeric micelle encapsulated cannabinoid using a dry-down or solvent evaporation method. For a discussion of the dry-down or solvent evaporation method and alternative methods by which a drug may be encapsulated by a polymeric micelle, see Cholkar, et al, *Recent Patents on Nanomedicine,* 2:82-95 (2012), which is incorporated herein by reference insofar as relates to methods and materials for encapsulation of drugs using polymeric micelles. The solvent evaporation method comprises dissolving an amphiphilic copolymer and a cannabinoid in a solvent followed by evaporation of the solvent to yield a film comprising the cannabinoid and the amphiphilic copolymer. Subsequent rehydration of the film using a preheated aqueous solution or water results in spontaneous formation of polymeric micelles encapsulating the cannabinoid. The method optionally includes sonication or filtration steps to ensure uniform particle size and/or removal of non-encapsulated drug. Thus, in various embodiments, the method for manufacture includes contacting a cannabinoid with an amphiphilic copolymer in a solvent, then preparing a dried film comprising the cannabinoid and the amphiphilic copolymer, and, finally, contacting the dried film with water or an aqueous solution to prepare a rehydrated composition comprising the cannabinoid encapsulated by polymeric micelles.

In various embodiments, the method for manufacture further includes sonication of the rehydrated composition to yield a polymeric micelle encapsulated cannabinoid suspension. In various embodiments, the method for manufacture further comprises filtering the polymeric micelle encapsulated cannabinoid suspension. In certain embodiments, the filtering is carried out using a filter having an average pore size of about or of at least about 100 nm, 110 nm, 120 nm, 130 nm, 140 nm, 150 nm, 160 nm, 170 nm, 180 nm, 190 nm, 200 nm, 210 nm, 220 nm, 230 nm, 240 nm, 250 nm, 260 nm, 270 nm, 280 nm, 290 nm, 300 nm, 350 nm, 400 nm, or 450 nm. In certain embodiments, the filtering is carried out using a filter having an average pore size of not more than about 100 nm, 110 nm, 120 nm, 130 nm, 140 nm, 150 nm, 160 nm, 170 nm, 180 nm, 190 nm, 200 nm, 210 nm, 220 nm, 230 nm, 240 nm, 250 nm, 260 nm, 270 nm, 280 nm, 290 nm, 300 nm, 350 nm, 400 nm, 450 nm, or 500 nm. In various embodiments, the filter has an average pore size of from about 100 nm to about 500 nm, from about 50 nm to about 500 nm, from about 200 nm to about 300 nm, or from about 120 nm to about 320 nm. In various embodiments, the filter is a nylon membrane filter.

In various embodiments, contacting the cannabinoid with the amphiphilic copolymer comprises dissolving the cannabinoid and the amphiphilic copolymer together in a solvent. In various embodiments, the solvent is an organic solvent or an inorganic solvent. In various embodiments, the solvent is dichloromethane, acetonitrile, or methanol. In certain embodiments, the method for manufacture further includes removing the solvent. The solvent can be removed by an evaporative process including evaporation under a vacuum or partial vacuum. In various embodiments, a concentration of the amphiphilic copolymer in the solvent is from about 8 mg/ml to about 16 mg/ml, from about 1 mg/ml to about 20 mg/ml, from about 1 mg/ml to about 100 mg/ml, from about 0.8 mg/ml to about 160 mg/ml, from about 5 mg/ml to about 20 mg/ml, or from about 5 mg/ml to about 50 mg/ml.

In some embodiments, contacting the cannabinoid with the amphiphilic copolymer comprises contacting the cannabinoid with the amphiphilic copolymer at a particular ratio (by weight) C:A of cannabinoid to amphiphilic copolymer. In various embodiments, the ratio C:A is from about 1:50 to about 50:1, from about 1:40 to about 40:1, from about 1:30 to about 30:1, from about 1:20 to about 20:1, or from about 1:10 to about 10:1. In various embodiments, the ratio of C:A is about 1:20. In various embodiments, the ratio C:A is from about 1:10 to about 1:30, from about 1:5 to about 1:50, from about 1:15 to about 1:30, from about 1:15 to about 1:50, from about 1:20 to about 1:40, from about 1:20 to about 1:50, or from about 1:20 to about 1:100. In various embodiments, the ratio C:A is selected to ensure maximal encapsulation of the cannabinoid by the amphiphilic copolymer.

In some embodiments, the method for manufacture includes lyophilizing the polymeric micelle encapsulated cannabinoid suspension. In various embodiments, the lyophilizing yields a polymeric micelle encapsulated cannabinoid powder. The polymeric micelle encapsulated cannabinoid powder can be resuspended in a solution, an aqueous solution, or water to yield a dosage form comprising the polymeric micelle encapsulated cannabinoid.

In various embodiments, polymeric micelles encapsulating a cannabinoid may be prepared according to the method provided in U.S. Pat. No. 8,629,177 comprising the steps of 1) dissolving an amphiphilic copolymer and $\Delta^9$THC in supercritical, critical, or near critical carbon dioxide fluid, and 2) injecting a stream of the carbon dioxide fluid mixture into a deaerated solution comprising a crosslinking agent (e.g., polyvinyl acetate (PVA)) in a buffer to form particles or spheres.

In various embodiments, the method of the invention for manufacture is simplified relative to the method of U.S. Pat. No. 8,629,177 by including no step wherein a supercritical fluid is used. Further, in various embodiments, the composition does not comprise polyvinyl acetate (PVA), a cross-linker, or a curing agent. Also, in various embodiments, the method for manufacture includes no curing or crosslinking step.

In some embodiments, the polymeric micelles are formed by a simple dissolution, a dialysis, an oil-in-water emulsion, a lyophilization or freeze drying method, the solvent evaporation method, or various combinations thereof.

In various embodiments, a composition comprising the polymeric micelle encapsulated cannabinoid does not comprise heptane or isopropyl alcohol.

In various embodiments, the method includes physical entrapment of the cannabinoid within a core of a polymeric micelle formed by the amphiphilic copolymer.

Dosage Forms

In one aspect, the present invention provides for a dosage form comprising a therapeutically effective amount of cannabinoid encapsulated in polymeric micelles.

In various embodiments, the dosage form comprises about or at least about 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg, 11 mg, 12 mg, 13 mg, 14 mg, or 15 mg of cannabinoid. In various embodiments, the dosage form comprises no more than bout 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg, 11 mg, 12 mg, 13 mg, 14 mg, or 15 mg of cannabinoid. In some embodiments, the dosage form comprises from about 1 mg to about 15 mg of the cannabinoid. In various embodiments, the dosage form is a liquid and comprises the cannabinoid at a concentration of from about 0.1 mg/ml to about 16 mg/ml, from about 1 mg/ml to about 5 mg/ml, from about 1 mg/ml to about 10 mg/ml, or from about 0.1 mg/ml to about 10 mg/ml.

In various embodiments, the dosage form is a liquid, a liquid suspension, or a powder. In various embodiments, the powder comprises lyophilized polymeric micelles encapsulating a therapeutically effective amount of cannabinoid.

In certain embodiments, the dosage form is suitable for intranasal delivery. In particular embodiments, the dosage form is suitable for delivery by inhalation. In various embodiments, the dosage form comprises a suspension of the polymeric micelle encapsulated cannabinoid in water, an aqueous solution, or a polar solvent.

In some embodiments, the dosage form is a liquid suspension, a suspension, an emulsion, or a multiphasic composition. In various embodiments, the dosage form comprises an isotonic saline solution and a pharmaceutically acceptable buffer. In various embodiments, the dosage form is an aqueous liquid suspension comprising polymeric micelles encapsulating a therapeutically effective amount of cannabinoid.

The polymeric micelle encapsulated cannabinoid dosage form advantageously is not readily amenable to abuse (e.g., freebasing or heating of the dosage form for inhalation of cannabinoids). Advantageously, use of the dosage form intranasally results in the cannabinoid reaching the brain via an efficient and rapid route avoiding the lungs and a high or other forms of intoxication.

In various embodiments, the dosage form is formulated to penetrate the nasal mucus and adhere to the local epithelium to minimize mucociliary clearance and facilitate maximal intranasal cannabinoid uptake. In various embodiments, the dosage form targets the nasal mucosa or the olfactory mucosa.

In various embodiments the dosage form is a powder to be administered intranasally by inhalation. The powder may be disposed within a container such as a hard gelatin capsule or a blister package, or a multi-dose device. The capsule or blister may be ruptured or broached within an inhaler device (discussed further below), thereby enabling the powder to be inhaled.

In various embodiments, the dosage form comprises an inert carrier or excipient. In various embodiments, the dosage form comprises a weight percent of inert carrier or excipient of from about 0.1% to about 2.0%, from about 0.1% to about 99.9%, from about 0.1% to about 95%, from about 0.1% to about 90%, from about 0.1% to about 50%, from about 95% to about 99.99%, from about 97% to about 99.9%, or from about 75% to about 99.9%.

In various embodiments, the dosage form includes any of various additional pharmaceutically active compounds known in the art that may have an additive or synergistic effect in treating a condition when administered in combination with the cannabinoid. For example, in certain embodiments the cannabinoid is delivered concurrently with an analgesic, such as an opioid, in embodiments for treating acute pain without causing respiratory depression. In other embodiments the cannabinoid is delivered concurrently with melatonin, caffeine, or vitamin B12.

Methods of Treatment and Methods of Administration

In one aspect, the present invention provides for a method for treating pain and neurological diseases. In various embodiments the neurological disease is Alzheimer's disease. The method includes administering to a patient in need thereof a composition comprising a therapeutically effective amount of a cannabinoid, or a pharmaceutically acceptable salt or solvate thereof, and an amphiphilic copolymer comprising at least one hydrophilic component and at least one hydrophobic component. The cannabinoid is encapsulated by a polymeric micelle formed by the amphiphilic copolymer. The composition is suitable for nasal, intranasal, or inhalation delivery.

In various embodiments, the therapeutically effective amount of the cannabinoid is an amount effective to treat Alzeheimer's disease in a subject identified in need. In various embodiments, the therapeutically effective amount of the cannabinoid results in an observable or quantifiable reduction in β-amyloid plaques in a subject administered with the cannabinoid. In various embodiments, the therapeutically effective amount of the cannabinoid results in a reduction of signs or symptoms of Alzeheimer's disease in a subject administered with the cannabinoid composition. For example, in certain embodiments there is a reduction of amyloid beta protein aggregation in the brain. In certain embodiments there are indications of improved memory in the subject. Subjects may exhibit improved short-term memory, less agitation, and relief from sleeping disorders.

In various embodiments, the therapeutically effective amount of the cannabinoid is a daily dose of about or of at least about 1 mg, 1.5 mg, 2 mg, 2.5 mg, 3 mg, 3.5 mg. 4 mg. 4.5 mg. 5 mg, 5.5 mg, 6 mg, 6.5 mg, 7 mg, 7.5 mg, 8 mg, 8.5 mg, 9 mg, 9.5 mg, 10 mg, 11 mg, 12 mg, 13 mg, 14 mg, 15 mg, 16 mg, 17 mg, 18 mg, 19 mg, 20 mg, 25 mg, 30 mg, or 35 mg. In various embodiments the therapeutically effective amount of the cannabinoid is a daily dose of less than 1.5 mg, 2 mg, 2.5 mg, 3 mg, 3.5 mg. 4 mg. 4.5 mg. 5 mg, 5.5 mg, 6 mg, 6.5 mg, 7 mg, 7.5 mg, 8 mg, 8.5 mg, 9 mg, 9.5 mg, 10 mg, 11 mg, 12 mg, 13 mg, 14 mg, 15 mg, 16 mg, 17 mg, 18 mg, 19 mg, 20 mg, 25 mg, 30 mg, or 35 mg. In various embodiments, the daily dose of the cannabinoid is from about 1 mg to about 35 mg, from about 1 to about 15 mg, from about 1 to about 10 mg, from about 1 to about 5 mg, or from about 1 to about 2.5 mg. In various embodiments, the cannabinoid is administered once daily (QD). In various embodiments, the cannabinoid is administered twice daily (BID).

In various embodiments, the composition comprising a cannabinoid is administered to to treat any condition in a subject for which a cannabinoid is indicated. In certain embodiments, the composition can be administered to a pediatric patient under the age of 18 or to an adult of age 18 or older.

In various embodiments, administration of the composition results in targeted delivery of the cannabinoid to the brain. In some embodiments, administration of the composition results in preferential delivery of the cannabinoid to a particular brain region. In various embodiments, the particular brain region is the olfactory complex, the entorhinal cortex, the hippocampus, the frontal cortex, or the back cortex. In various embodiments, preferential delivery to the particular brain region is measured as a higher concentration of the cannabinoid or a metabolite thereof within the particular brain region relative to alternative brain regions after 5 min, 10 min, 15 min, 20 min, 25 min, 30 min, 45 min, 1 hour, 2 hours, or a combination thereof. In various embodiments, administration of the composition results in a higher concentration of the cannabinoid or metabolites thereof in the brain relative to concentrations in the blood after 5 min, 10 min, 20 min, 25 min, 30 min, 45 min, 1 hour, or 2 hours.

In various embodiments, administration of the composition to a subject results in controlled metabolic processing of the cannabinoid by the subject over time. In certain embodiments the controlled metabolic processing comprises a slowed rate of conversion of the cannabinoid to metabolites thereof relative to compositions that do not comprise a polymeric micelle encapsulated cannabinoid. In various embodiments, the controlled metabolic processing is measured as a higher concentration of OH-THC than COOH-THC in a particular brain region, in the brain, or in blood of the subject after 5 min, 10 min, 15 min, 20 min, 25 min, 30 min, 35 min, 40 min, 45 min, 50 min, 1 hour, or 2 hours.

In various embodiments, a therapeutic result, comprising a reduction in a symptom associated with any of the conditions listed above, is observed within about 15 min, 20 min, 25 min, 30 min, 45 min, 1 hour, 1.5 hours, 2 hours, 12 hours, or 24 hours of administering the composition. In certain embodiments, the therapeutic result is a dissolution of β-amyloid plaques, an improvement in memory, inhibition of β-amyloid synthesis, inhibition of plaque formation, or down-regulation of GSK-3β and/or pGSK-3β, or a reduction in a symptom associated with any of the conditions listed above.

In various embodiments, the compositions of the present invention are delivered intranasally. Intranasal administration of a cannabinoid advantageously allows the cannabinoid to bypass the blood-brain barrier. Intranasal administration of the compositions maximizes the chance of the cannabinoid reaching the brain.

In various embodiments, the composition is administered to a subject using a device for intranasal delivery of the composition. In various embodiments, the device for intranasal delivery is a nasal pump spray or a dropper. In some embodiments, the composition is delivered intranasally by inhalation of a nebulized liquid- or powder-based aerosol. In some embodiments, the device is an electronic atomizer or a bidirectional breath-powered nasal delivery device. In some embodiments, the device is OPTIMIST (Djupesland, et al., *Laryngoscope,* 116:466-72 (2006), the disclosure of which is incorporated herein by reference to provide examples of intranasal delivery devices) or VIANASE (Giroux, et al., *Drug Delivery Technology,* 5:44-49 (2005), the disclosure of which is incorporated herein by reference to provide examples of intranasal delivery devices). In some embodiments, the device is a PRECISION OLFACTORY DELIVERY (POD) device (Shrewsbury, et al., *Headache,* 59:394-409 (2019)). In various embodiments, the device delivers the composition into the upper nasal cavity. In various embodiments, the device is a squeeze bottle or a manual or electrically powered intranasal pump dispenser. In various embodiments, the delivery device comprises a nebulizer or a pressurized aerosol generator. In various embodiments, the delivery device administers a liquid or powder to the nasal mucosa.

In various embodiments, the composition comprises a propellant. In some embodiments, the propellant is a hydrofluoroalkane (HFA). HFA propellants are volatile, non-toxic, non-flammable, and environmentally friendly, which makes them an excellent delivery vehicle for spray formulations. In some embodiments, the propellant is a hydrofluoroalkane selected from 1,1,1,2-tetrafluoroethane (HFC-134a) and 1,1,1,2,3,3,3-Heptafluoropropane (HFC-227), and combinations thereof.

In various embodiments, administration of the polymeric micelle encapsulated cannabinoid to a subject does not result in intoxication of the subject or the experience of a high.

Kits

The present invention provides for kits for use in treating pain and neurological diseases. The kits comprise one of the compositions or dosage forms described above, optionally disposed within a suitable delivery device. The delivery device is a device for intranasal delivery, such as a device described above. In various embodiments, the kit comprises instructions explaining a method and frequency for intranasal administration of the composition. In various embodiments, the kit includes information relating to safety and ingredients of the composition disposed within the delivery device.

In various embodiments, the kit comprises a lyophilized powder comprising a cannabinoid encapsulated by polymeric micelles. In certain embodiments, the kit includes a solution within which to suspend the cannabinoid encapsulated by polymeric micelles prior to administration.

In certain embodiments, the delivery device is a device for delivery of a lyophilized powder to a subject intranasally.

In some embodiments, use of the kit comprises suspending a lyophilized powder comprising a cannabinoid encapsulated by polymeric micelles in a solution or solvent, optionally in a part of the kit, to yield a suspension and then disposing the suspension within the delivery device.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Many modifications and variations of the invention may be apparent to those skilled in the art upon reading this specification, and such variations can be made without departing from the invention in spirit or in scope. The invention is to be limited only by the appended claims, including the full scope of equivalents to which those claims are entitled.

The following materials and methods were used, unless described otherwise in a specific Example.

Materials and Methods

Drug Administration

The cannabinoid used as an active ingredient in these Examples was $\Delta^9$-THC. In the following examples, doses of 0.2 mg/kg were delivered to mice, based on mouse weight. (A suitable dose for mice typically is from about 0.2 to about 0.3 mg/kg.) The mice were selected from strains C57B6, SJL, and B6D2F1, or a mix of these strains. Strain C57B6 is generally preferred, although any suitable mouse strain may be used. For example, a 50-gram mouse was dosed with 6.25 μL of one of the below described 1.6 mg/ml $\Delta^9$-THC formulations. If a mouse was administered less than 3 ul of the 1.6 mg/ml liquid, the whole dose was delivered by pipetting to the left nostril in one second. If more than 3 ul was administered, the total volume was pipetted from the 1.6 mg/ml $\Delta^9$-THC formulation and then dispensed to the left nostril in two drops until the entire volume was dispensed. The dispensed $\Delta^9$-THC treatments from the pipette tip were in such a small volume that the liquid formulations bubbled at the tip of the pipette and were then taken into the mouse nasal cavity during mouse inhalation. The pipette tip never touches the mouse's nose directly.

To deliver a dose of drug, a mouse was gently grabbed by the scuff of the neck and stabilized with the mouse belly facing upwards. The mouse's nose was maintained parallel to a level planar surface. The formulation was then pipetted into a droplet at the end of the pipette tip. This droplet was then dropped to the left nostril of the mouse. The pipette tip itself never touched the nose of the mouse directly. The mouse was held in position with the nose maintained parallel to the level surface for 30 seconds. After 30 seconds, the mouse was then returned to a cage. This same procedure just described is followed to administer a formulation at a volume greater than 3 μl with the modification that the formulation is pipetted into the nose in separate droplets until the full volume greater than 3 μl has been administered.

Liquid Chromotography (LC) Tandem Mass Spectrometry (MS/MS) (LC/MS/MS)

5.0-5.5 mg of different brain tissue regions (Front Cortex (OFC), Hippocampus (HPC), Olfactory) were used for LC/MS/MS. 350-375 ul of whole blood were used for LC/MS/MS.

Samples were prepared for LC/MS/MS as follows. For brain tissue samples, samples were thawed at 37° C. and then ground in 200 μl PBS for 30 s followed by sonication for 10 sec at 60% power. The sonicated brain tissue sample was then diluted with about 600 μl water to a final volume of 800 μl and transferred to a glass tube to yield presample. For whole blood samples, samples were thawed at 37° C. and then sonicated for 10 s at 60% power. The sonicated blood samples were transferred to glass tubes and diluted with water to a final volume of 800 μl to yield a presample.

Next, 200 μl 10% acetic acid was added to each presample and vortexed. To the resulting solution was added 2,000 μl 9:1 hexane:ethyl acetate solution followed by mixing on a rotator for 45 min. Next, the mixed solution was centrifuged at 2,800×g for 15 min at 15° C. Following centrifugation, a resulting upper (organic) layer was transferred to a 2 ml vial and dried completely at 37° C. under nitrogen gas. The resulting dried composition was reconstituted in 40 μl of a 50:50 solution of acetonitrile:water by vortexing to yield a prepared sample. The prepared sample was then analyzed using LC/MS/MS.

Prepared samples and calibration samples were analyzed using LC/MS/MS at a flow rate of 0.45 ml/min and a final injection volume of 15 μl.

LC/MS/MS was conducted using an Agilent Technologies 6460 Triple quad LC/MS, model no. G6460A. The following software was used: Agilent Technologies MassHunter Workstation Software LC/MS Data Acquisition for 6400 Series Triple Quadrupole Version B.05.00, Build 5.0.5027.0 and AgilentTechnologies MassHunter Workstation Software Qualitative Analysis Version B.05.00, Build 5.0.519.0.

All LC/MS/MS results are based on concentrations in the 40 μl reconstituted samples and the mass or volume of the brain tissue or blood, respectively, used to prepare each sample. "Total drug" indicates a summation of $\Delta^9$-THC, OH-THC, and COOH-THC values calculated for a sample(s). Control mice had no detected $\Delta^9$-THC metabolites at any time point evaluated in any experiment.

Statistical Analysis

All statistical analyses were conducted using Prism Graph Pad 8.0.

Measuring Average Size of Polymeric Micelles Using Dynamic Light Scattering (DLS)

DLS was used to measure a size distribution of the polymeric micelles and the nano-emulsion particles. A ZetaSizer nano series machine (nano-ZS90) was used in combination with ZetaSizer Software to measure and calculate a size distribution.

The following protocol was followed to measure the size distribution of the polymeric micelles using DLS. A 100 μl polymeric micelle sample was diluted in 100 μl distilled, deionized water to yield a diluted sample. The diluted sample was loaded into a DLS cuvette and inserted into the Zetasizer nano series machine. The Zetasizer application was then executed using the following parameters: Measure=manual; Measurement type=size; Dispersant type=water; Temperature=25° C. A similar protocol was uses to measure the size distribution of nano-emulsion particles.

Table 3 below and FIG. 1 provide results obtained according to the above DLS protocol for a representative sample of the polymeric micelle encapsulated $\Delta^9$-THC formulation prepared according to embodiments of the invention. The polymeric micelles of the representative sample had an average diameter of about 142.6 nm.

TABLE 3

Zetasizer application output for DLS measurement of a representative sample of the polymeric micelle encapsulated $\Delta^9$-THC formulation prepared according to embodiments of the invention.

| | | | | | |
|---|---|---|---|---|---|
| Material RI: 1.54 | | Dispersant Name: Water | | | |
| Material Absorption: 0.000 | | Dispersant RI: 1.330 | | | |
| Temperature (° C.): 25.0 | | Viscosity (cP): 0.8872 | | | |
| Count Rate (kcps): 40.9 | | Duration Used (5): 150 | | | |
| Cell Description: Disposable sizing cuvette | | Measurement Position (mm): 4.65 | | | |
| | | Attenuator: 11 | | | |
| | | | Size (d · nm): | % Intensity: | St Dev (d · nm): |
| Z-Average (d · nm): | 129.9 | Peak 1: | 142.6 | 97.1 | 71.40 |
| PdI: | 0.402 | Peak 2: | 5364 | 2.9 | 332.4 |
| Intercept | 0.972 | Peak 3: | 0.000 | 0.0 | 0.000 |
| Result quality: | Good | | | | |

Example 1—Nano-Emulsion Formulation

In this example, $\Delta^9$-THC was added to an oil phase, which was then combined with a water phase, to form an emulsion. (THC is more soluble in oil than in water.) The emulsion was sonicated to provide nano-size particles. Compositions of an oil phase mixture and a water phase mixture used in preparation of the nano-emulsion formulation are provided in Table 1.

TABLE 1

| Ingredient | Approximate % Volume (of 20 ml total) | Quantity for 20 ml batch |
|---|---|---|
| $\Delta^9$-THC | | 32 mg (0.219 ml) |
| Fish oil | 10% | 2.0 ml |
| MCT | 10% | 2.0 ml |
| Coconut oil | 5% | 1.0 ml |
| Lecithin/Emulsifying agents | 5% | 1.0 g |
| Methyl Paraben (pfaltz & Bause 5026-62-0) | 1% | 0.2 g |
| Propyl Paraben (pfaltz & Bause 35285-69-9) | 1% | 0.2 g |
| Pluronic F 68 (MP 2750016) | 1% | 0.2 g |
| Glycerine (fisher 56-81-5) | 2.5% | 0.5 ml |
| PEG 400 (fisher p167-1) | 5% | 1.0 ml |
| Purified Water | ~66% | ~13.2 ml |

To prepare the nano-emulsion formulation, the oil phase mixture was first prepared. Coconut oil (Carrington Farms, pure, unrefined, cold pressed) was melted at 37° C. in a water bath. 1.0 g of Lecithin (Fisher, 03376-250, Lot 153621) was weighed out. 2 ml MCT (Now Sports, 100% pure MCT oil) was added to the Lecithin to yield the oil phase mixture. 2 ml of fish oil (Carlson the Finest Norwegian Fish oil, lemon taste) was added to the oil phase mixture. 1 ml of coconut oil was then added to the oil phase mixture. The oil phase mixture was then stirred at 200 rpm in a 500 ml glass beaker at 37° C. for 2 hours using a stir mixer until all added ingredients dissolved. The beaker was covered with plastic wrap. Once the ingredients of the oil phase mixture dissolved, the oil phase mixture was stirred for about 12 hours (e.g. overnight) at room temperature. Then, 220 of $\Delta^9$-THC (1-7370-7554, 145.9 mg/ml stock), which corresponded to 32 mg $\Delta^9$-THC, was added to the oil phase mixture. The oil phase mixture was then stirred at 200 rpm at room temperature for an hour.

The water phase mixture was then prepared by combining in a 50 ml conical tube 1 ml polyethylene glycol (PEG 400) (Sigma P-3265, lot 81K0326), 0.5 ml glycerol (Sigma G5516-1L, lot SHBD3108V), 0.2 g sodium methyl paraben (Pfaltz and Bause, item number 506130, lot 18552, cas #5026-62-0), 0.2 g propylparaben sodium (Spectrum P1457, lot 2EC0375), 0.2 g Pluronic F68 (MP Biomedicals, A1288.0500, lot 5X010736, CAS 9003-11-6), and enough water to make a total volume of the water phase mixture 14 ml. The water phase mixture was shaken at room temperature for 30 minutes.

The oil phase mixture and the water phase mixture, both prepared as described above, were then combined in a 50 ml conical tube to yield an emulsion composition. Water was added to the resulting emulsion composition to bring a total volume of the emulsion composition to 20 ml. The emulsion composition was then vortexed (VWR Model: G560) for 20 minutes at maximum speed. The emulsion composition was then emulsified by three 11-minute cycles of sonication in an ice bath allowing the emulsion composition to cool between each 11-minute cycle. The sonication cycles produced the nano-emulsion formulation. The sonication protocol was 54 s pulse on, 6 s pulse off, with an amplitude of 90%. The sonicator was Model FB120 from Fisher Scientific: 120 W, 120V, 50/60 Hz NOM, Frequency: 20 kHz, Full Size: 3A SL0-BLD.

The final working concentration of $\Delta^9$-THC in the nano-emulsion formulation was 1.5 mg/ml in a 20 ml final volume. The nano-emulsion formulation was stored at 4° C. The average particle size for the nano particles was about 215.2 nm.

Example 2—Polymeric Micelle Encapsulated A9-THC Formulations

In this example, a cannabinoid was encapsulated in an amphiphilic copolymer, to form a "poly" composition. A polymeric micelle encapsulated $\Delta^9$-THC formulation was prepared using poly(ethylene glycol) methyl ether-block-poly(lactide-co-glycolide) (PEG-PLGA), having number average molecular weights, respectively, of PEG 2000 and PLGA 4500 (total average 6500) (Sigma Aldrich. Cat #: 764825-1G).

The polymeric micelle encapsulated $\Delta^9$-THC formulation was prepared as follows. A PEG-PLGA polymer comprising PEG (Mn=2000) and PLGA (Mn=4500) from Sigma-Aldrich, Product No. 764825. $\Delta^9$-THC (Sigma, Cat #: T4764-1ML) was dried using nitrogen gas at 37° C. for 5 min or until completely dried (max 10 min). Next, 1 mg of the $\Delta^9$-THC and 10 mg of the PEG-PLGA polymer were dissolved in dichloromethane (5-10 ml max). Organic solvent was then removed by rotary evaporation under reduced pressure to form a dried film.

The dried film was hydrated with distilled water pre-warmed to 50° C. to yield a suspension. The suspension was then sonicated at 50% power for 10 min using a protocol of 10 s on and 10 s off to yield Δ$^9$-THC encapsulated polymeric micelles in solution. The sonicator used for sonication was a Fisher Scientific model FB120, 120 W, 120V, 50/60 Hz NOM, 20 kHz sonicator with a full size of 3A SL0-BLD. Non-incorporated reagents were separated by filtration through a 220 nm nylon membrane (Novatech cat #371-2215-OEM) and the filtered micelle solution was subjected to characterization, freeze-drying or both.

For freeze-drying, 0.5 ml of filtered micelle solution was transferred to 5 ml glass vials and frozen at −20° C. in a freeze-dryer. Frozen product was then lyophilized under 10 kPa negative pressure for 2 hr to yield a lyophilized product. After freeze-drying, vials were stoppered and stored at 4° C.

The polymeric micelle encapsulated Δ$^9$-THC formulation was prepared by suspending the lyophilized product in water to a final concentration of 1.6 mg/ml Δ$^9$-THC and sonicating until clear using the sonication protocol and sonicator described above.

Example 3—Water-Based Δ$^9$-THC Formulation

A water-based liquid composition (50 ml batch) comprising Δ$^9$-THC was prepared by combining Mixture I and Mixture II, as provided in Table 2.

TABLE 2

| Mixture I (90 vol % of water-based formulation) | Approximate % Volume (of 20 ml total) | Quantity for 45 ml batch of stock solution |
|---|---|---|
| Polyethylene glycol 400 | 12% | 6 ml |
| Methyl Paraben | 0.4% | 0.2 g |
| Propyl Paraben | 0.4% | 0.2 g |
| Sucralose | 0.05% | 25 mg |
| Butylated Hydroxyanisole | 0.05% | 25 mg |
| Water ($H_2O$) | ~87.1% | ~38.6 ml |
| **Mixture II (10 vol % of water-based formulation)** | **Approximate % Volume (of 5 ml total)** | **Quantity for 5 ml batch of stock solution** |
| Δ$^9$-THC | 550 ul | 80 mg (550 ul) |
| ETOH | 1% | 500 ul |
| Propylene glycol | 5.5% | 2.75 ml |
| $H_2O$ | ~93.5% | ~1.67 ml |

To prepare the water-based Δ$^9$-THC formulation, Mixture I was prepared in a 50 ml conical tube, by dissolving (a) 3.6 ml polyethylene glycol (PEG 400) (Sigma P-3265, lot 81K0326), (b) 0.12 g sodium methyl paraben (Pfaltz and Bause, item number 506130, lot 18552, cas #5026-62-0), (c) 0.12 g propylparaben sodium (Spectrum P1457, lot 2EC0375), (d) 15.0 mg Sucralose 98% powder (Alpha Aesar J66736, lot T21D050), and (e) 15.0 mg Butylated Hydroxy-anisole (MP Cat. No. 101159, lot QR11576) in enough water to bring the final volume of the resulting Mixture I to 30 ml. This was mixed on a shaker at room temperature for 10 minutes.

Mixture II was prepared by combining (i) 54.8 µl of Δ$^9$-THC stock comprising 145.9 mg/ml Δ$^9$-THC in heptane/IPA (8.0 mg Δ$^9$-THC total) with (ii) 50 µl ethanol, 275 µl propylene glycol, and (iii) 120.2 µl water in a test tube. The resulting Mixture II was then vortexed.

The water-based Δ$^9$-THC formulation was then prepared by combining 4.5 ml of Mixture I with ~0.5 ml Mixture II to a final volume of 5 ml in a test tube. The test tube was then inverted to mix and yield the water-based Δ$^9$-THC formulation. The final concentration of Δ$^9$-THC in the water-based Δ$^9$-THC formulation was 1.6 mg/ml.

Example 4—Oil-Based Δ9-THC Formulation

An oil-based liquid Δ$^9$-THC composition was prepared in this example. An oil-based solution was obtained from Yunnan TIANFU Inc. in China. The solution is a proprietary mixture of tea extract, walnut extract, lingzhi mushroom, and a coffee extract. To 494.5 µl the proprietary mixture was added 5.5 µl of a Δ$^9$-THC stock comprising 145.9 mg/ml Δ$^9$-THC in heptane/IPA (800 µg Δ$^9$-THC total) to yield the oil-based Δ$^9$-THC formulation. The oil-based Δ$^9$-THC formulation was inverted ~5 times to mix.

Example 5—Naked Δ9-THC Formulation

A "naked" Δ$^9$-THC formulation was prepared as follows. A Δ$^9$-THC in heptane/IPA solution was obtained from Rhodes Technologies at a 14.6% concentration (1-370-7554). The Δ$^9$-THC in heptane/IPA solution was diluted to a final concentration of 1.5 mg/µl in PBS.

Example 6—Administration Δ$^9$-THC Formulation to Mice

An experiment was conducted to compare the distribution of Δ$^9$-THC and Δ$^9$-THC metabolites in mice following administration of (alternatively, "treatment with") each of four compositions: (1) the naked Δ$^9$-THC formulation (naked), (2) the oil-based Δ$^9$-THC formulation (oil), (3) the water-based Δ$^9$-THC formulation (liquid), and (4) the nano-emulsion formulation (nano). Following administration of each formula, mice were sacrificed after 15 min, 30 min, 45 min, and 2 hrs. Blood samples (375 µl) were collected by intracardial punctuation, and brains were removed and dissected into different regions: olfactory cortex (OFC), front and back cortex (collectively CTX), and hippocampus (HPC). Each brain tissue sample was 5.5-5.5 mg.

Six mice were administered each of the five formulations (n=6 for each formulation), and one control group (n=3) was not administered any of the formulations. The formulations were each delivered by intranasal delivery.

Measurements Taken 15 Minutes after Formulation Administration

Figure 2A:
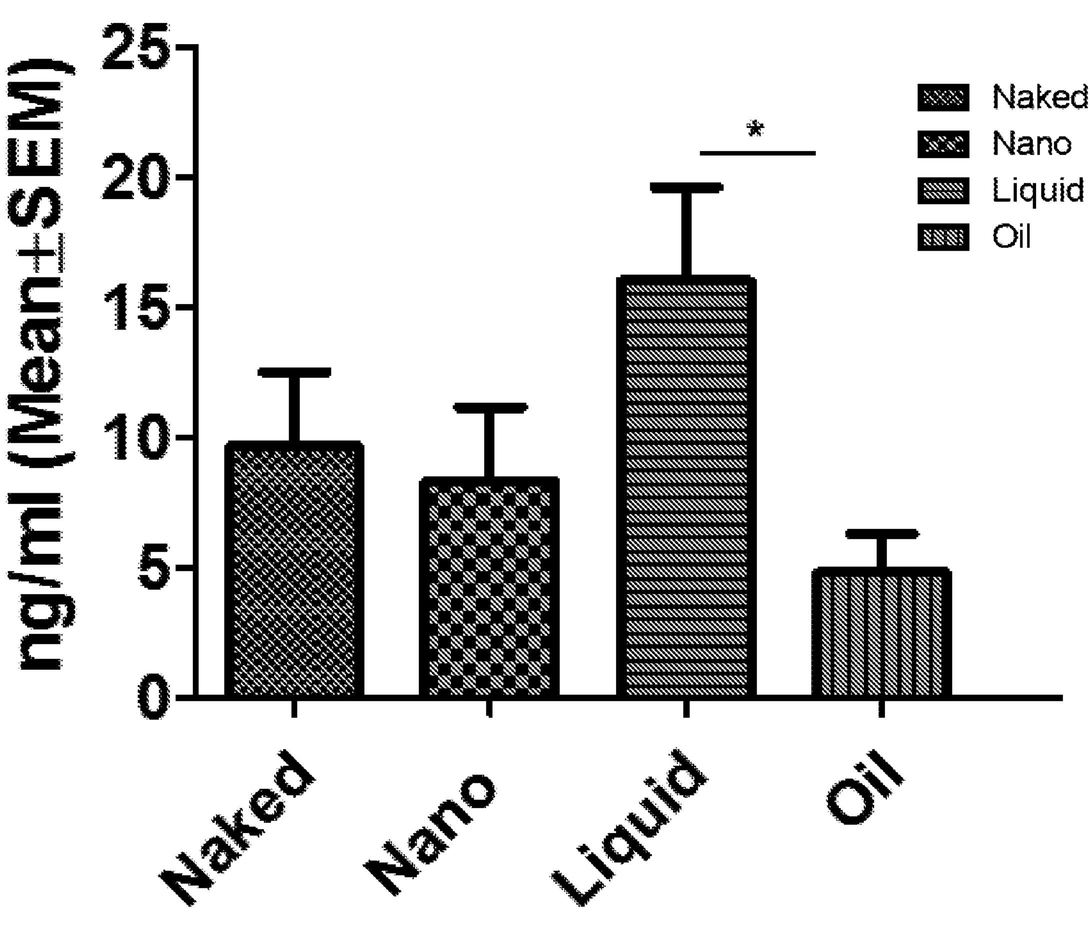
FIGS. 2A-2C show total $\Delta^9$-tetrahydrocannabinol ($\Delta^9$-THC) levels in blood and brain tissues 15 minutes after intranasal delivery and total drug distribution in the brain for each indicated formulation.
Figure 2B:
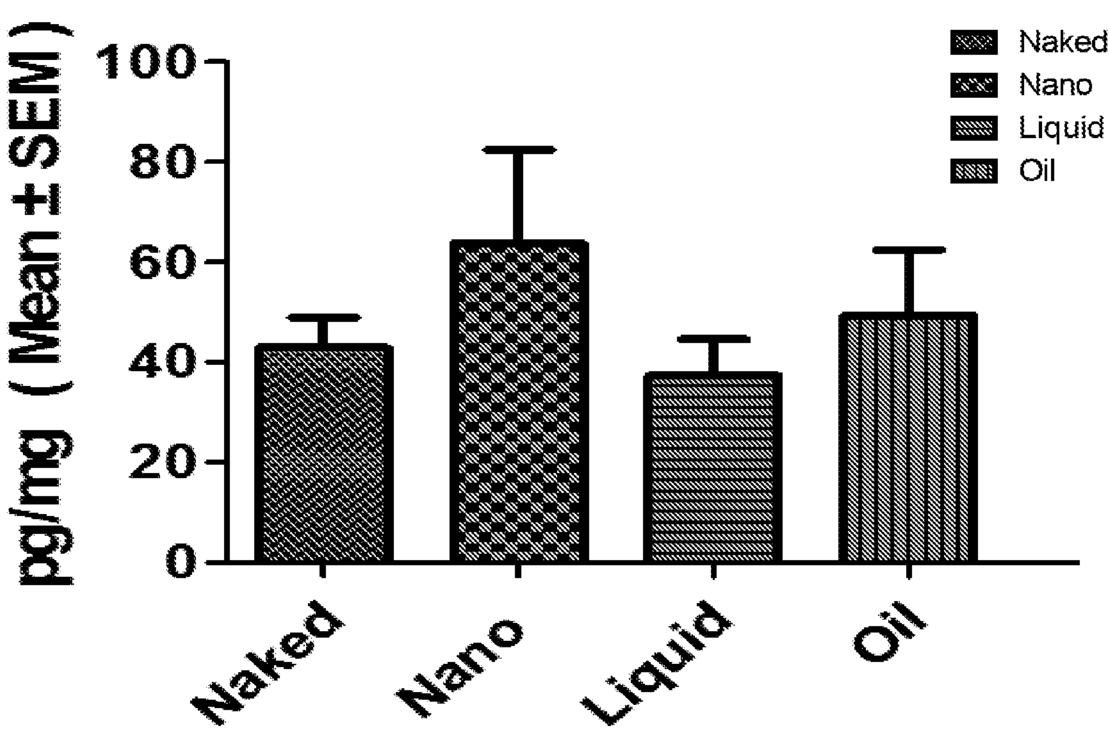
Figure 2C:
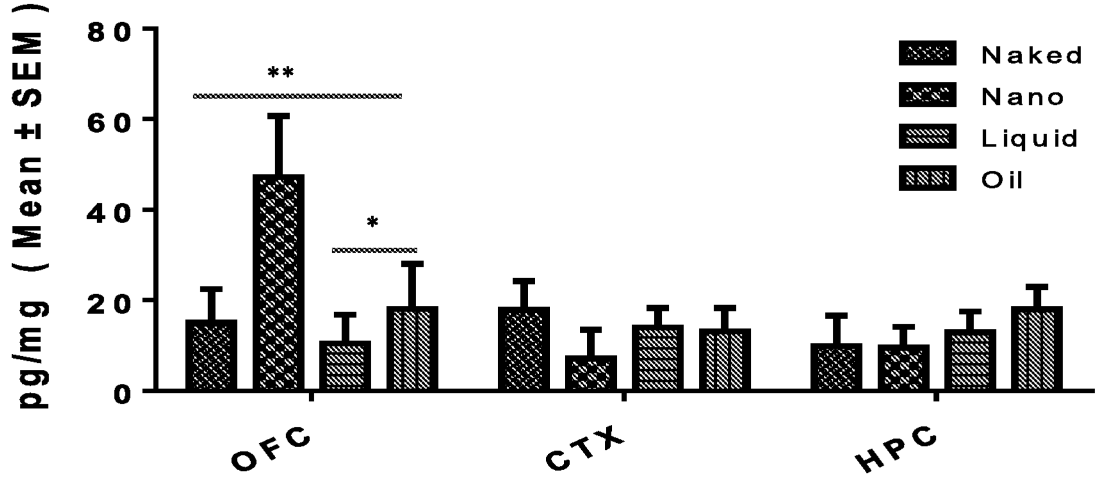

All Δ$^9$-THC formulation treatments resulted in detectable drug levels at 15 min after intranasal administration, see FIGS. 2A-2C. The liquid Δ$^9$-THC formulation treatment resulted in higher total drug levels than the oil formulation, however there was no significant difference between the liquid formulation and any of the other formulations or between any of other formulations (n=6, $p<0.05$), see FIG. 2A. There was also no significant difference between detected drug levels between the formulations in the brain after 15 minutes. (n=6, $p<0.05$), see FIG. 2B. After 15 minutes, there was no significant difference between formulations in CTX or HPC, see FIG. 2C. However, in OFC, the nano-emulsion group had significantly higher levels of total drug than naked Δ$^9$-THC, liquid Δ$^9$-THC, and oil-based Δ$^9$-THC ($p<0.05$), see FIG. 2C.

Figure 3A:
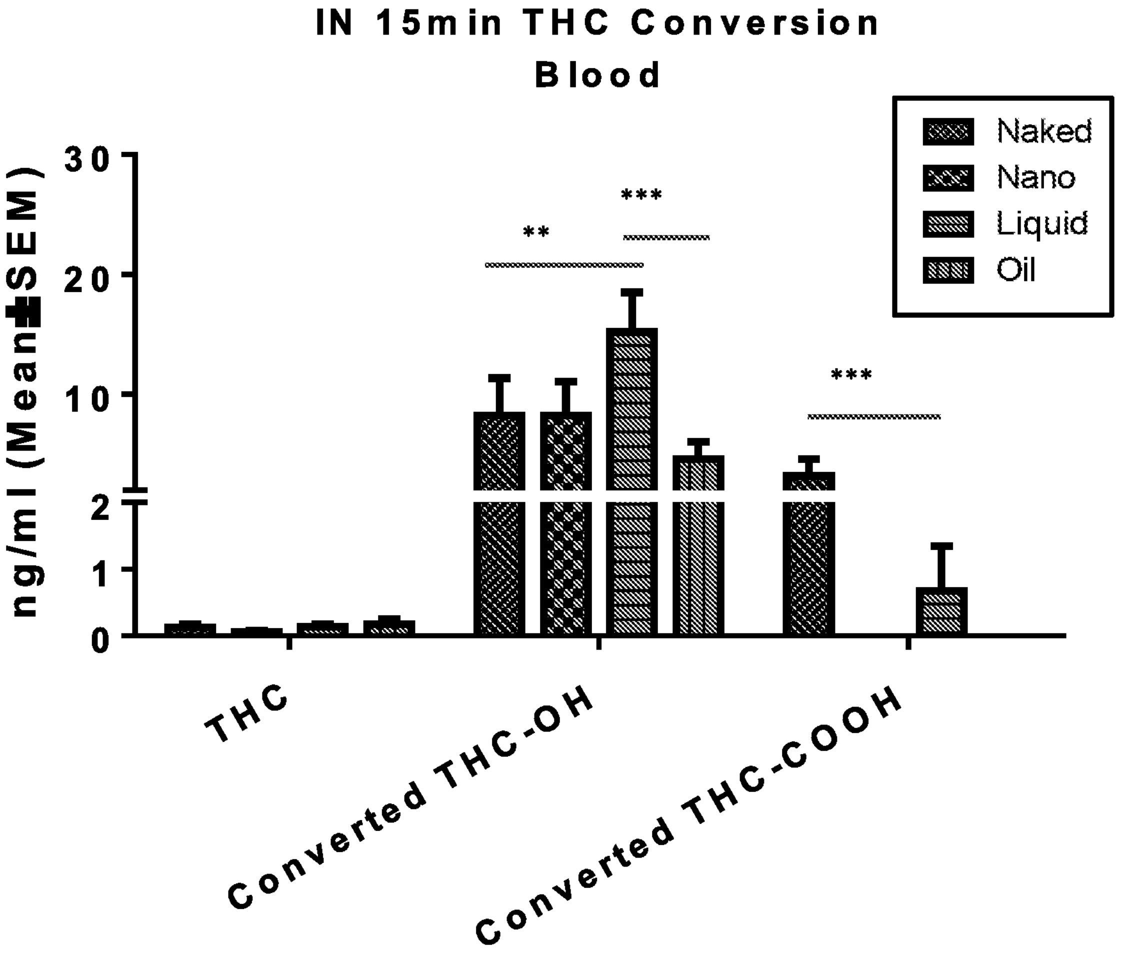
FIGS. 3A-3B show the conversion of $\Delta^9$-THC to its metabolites: 11-OH-THC (aka, OH-THC or THC-OH; 11-hydroxy-$\Delta^9$-tetrahydrocannabinol) and 11-COOH-THC (aka, COOH-THC or THC-COOH; 11-nor-9-hydroxy-$\Delta^9$-tetrahydrocannabinol) for each indicated formulation 15 min after intranasal delivery.
Figure 3B:
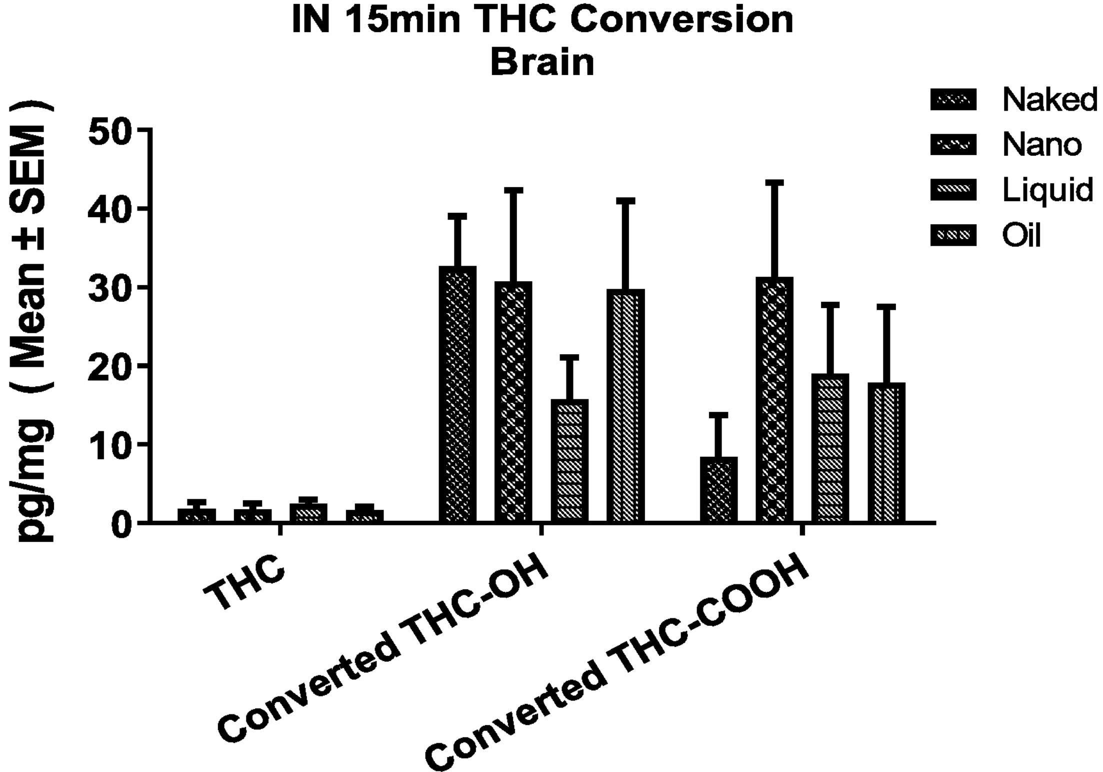

Compared with the other formulations, the liquid-THC formulation treatment had a higher level of converted Δ$^9$-THC into OH-THC in whole blood when compared with naked $\Delta^9$-THC formulation and nano-emulsion $\Delta^9$-THC formulation ($n=6$, $p<0.01$) and when compared with oil-based $\Delta^9$-THC, see FIG. 3A. The higher level of $\Delta^9$-THC converted to THC-OH is a disadvantage of the liquid formulation. There were no significant differences between any of the formulations in the conversion of $\Delta^9$-THC to its metabolites in the brain tissues, see FIG. 3B.

Figure 4:
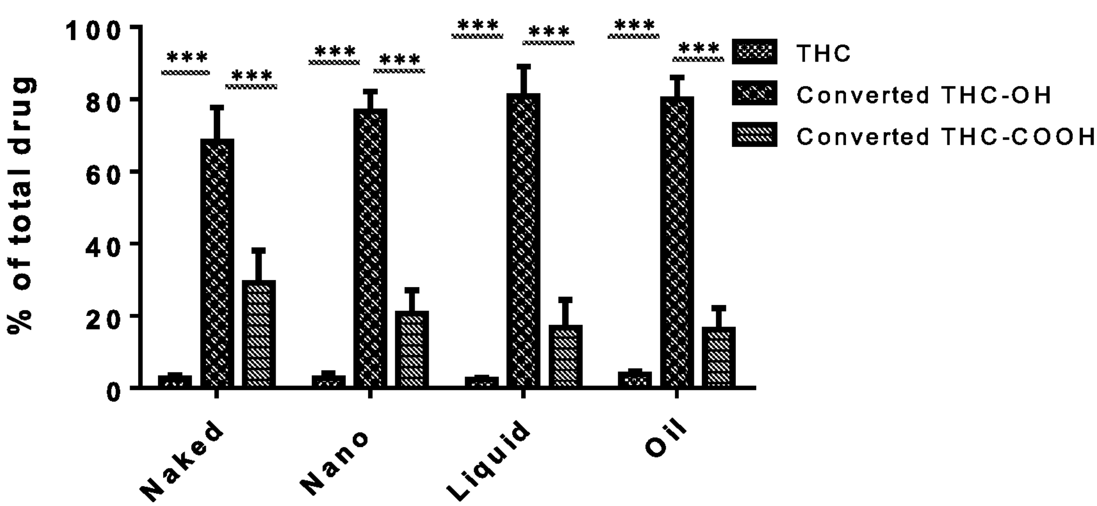
FIG. 4 provides a bar graph showing percentage of total $\Delta^9$-THC administered converted to its metabolites for each indicated formulation 15 min after intranasal delivery.

After 15 minutes, the majority of the $\Delta^9$-THC was converted into THC-OH, with small amounts of THC-COOH, and trace amounts of $\Delta^9$-THC left over ($n=6$, $p<0.001$), in all five compositions. See, FIG. 4.

Measurements Taken 30 Minutes after Formula Administration

Figure 5A:
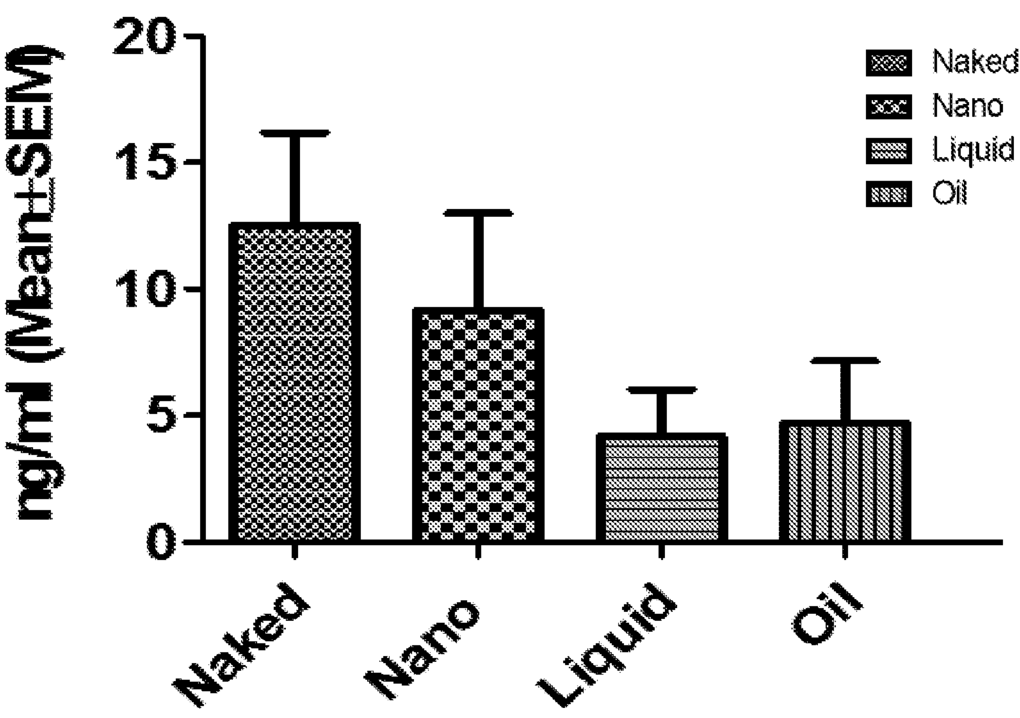
FIGS. 5A-5C show total drug ($\Delta^9$-THC and its metabolites) levels in blood and brain tissues for each indicated formulation 30 minutes after intranasal delivery, and drug distribution in brain tissues.
Figure 5B:
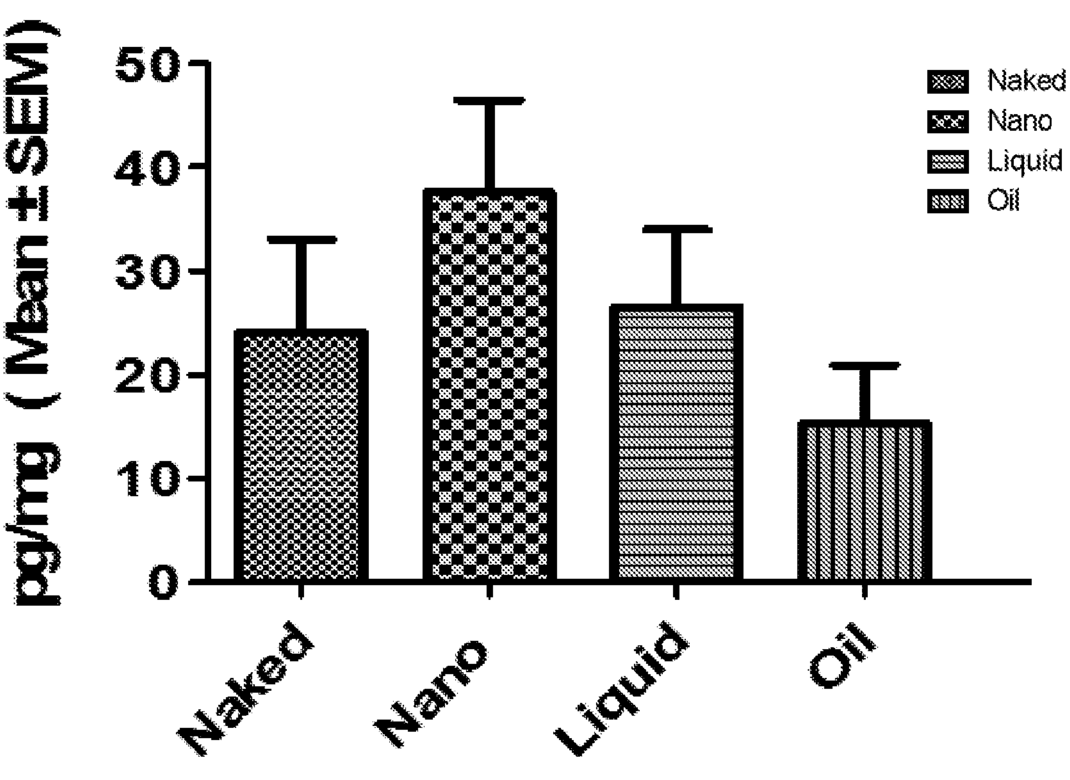
Figure 5C:
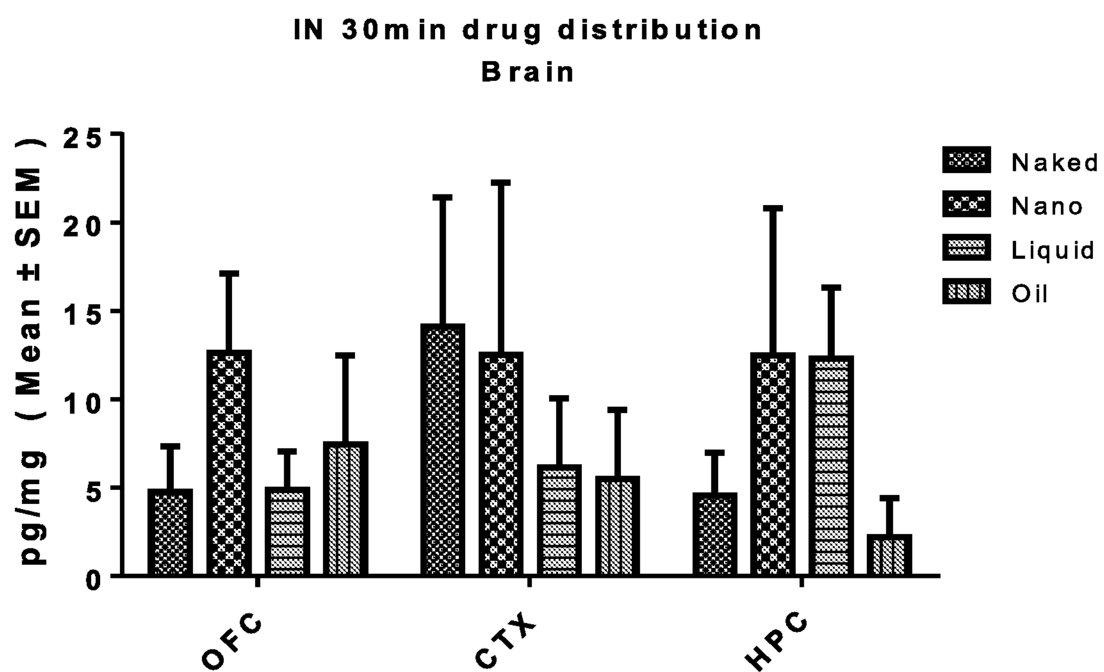

All $\Delta^9$-THC formulation treatments resulted in detectable total drug levels 30 min after intranasal administration. There was no significant difference between the detected levels of total drug between the formulations in blood, brain, or between brain regions. ($n=6$, $p<0.05$), as shown in FIGS. 5A-5C.

Figure 6A:
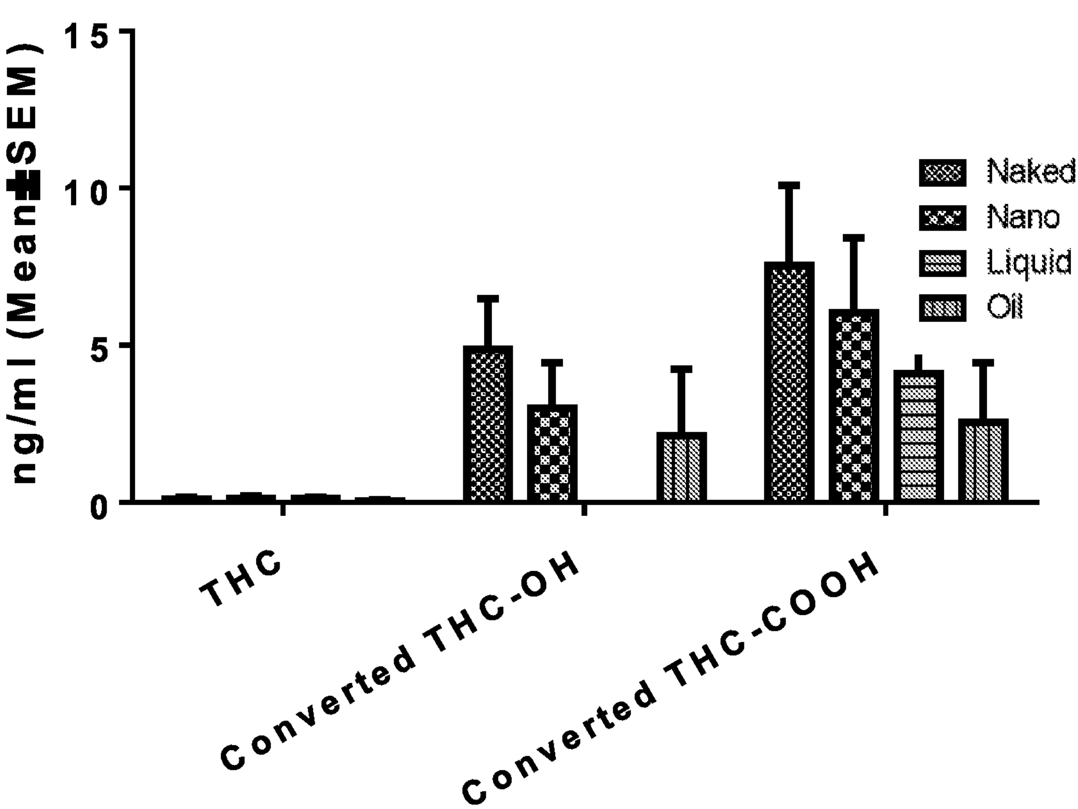
FIGS. 6A and 6B show conversion of $\Delta^9$-THC to its metabolites OH-THC and COOH-THC for each indicated formulation 30 min after intranasal delivery.
Figure 6B:
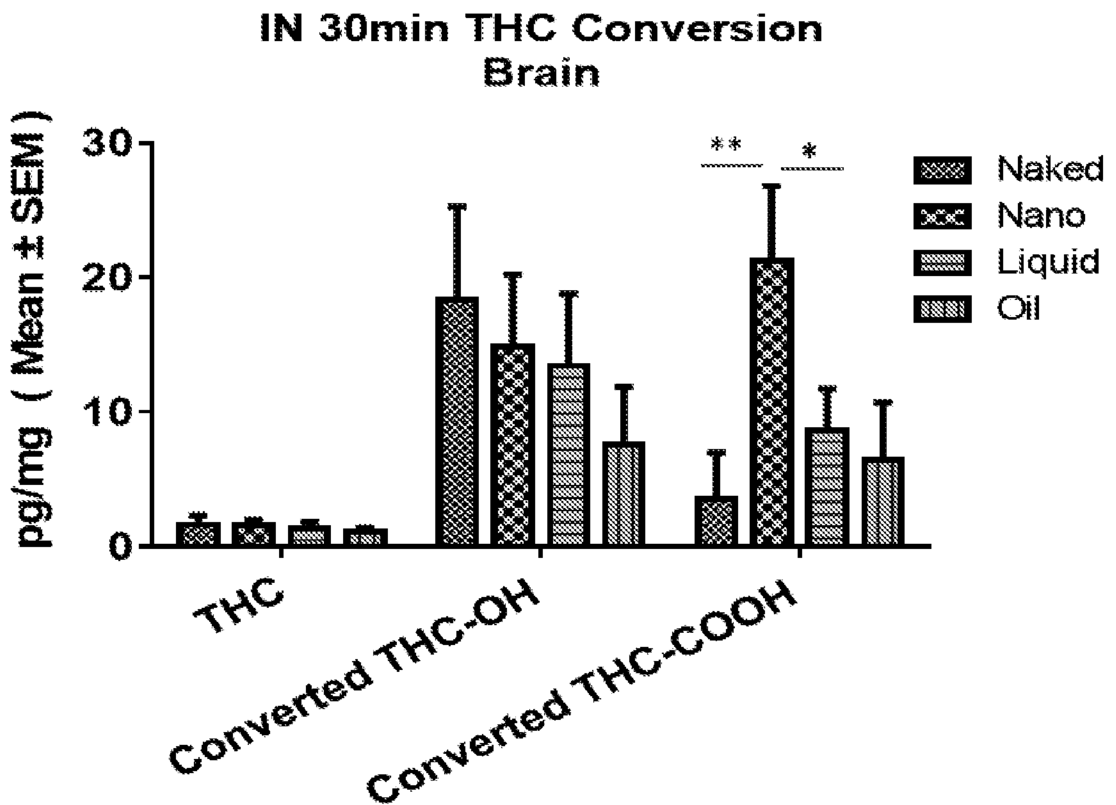

After 30 minutes there was no significant difference between any of the groups in conversion of $\Delta^9$-THC into its metabolites in whole blood, see FIG. 6A. There was a trace amount of remaining $\Delta^9$-THC, some THC-OH, and increasing amounts of THC-COOH, see FIG. 6A. In brain tissues, nano-THC treatment exhibited significantly higher amounts of THC-COOH compared to naked $\Delta^9$-THC ($p<0.01$) and the oil-based $\Delta^9$-THC formulation ($p<0.05$), see FIG. 6B.

Figure 7:
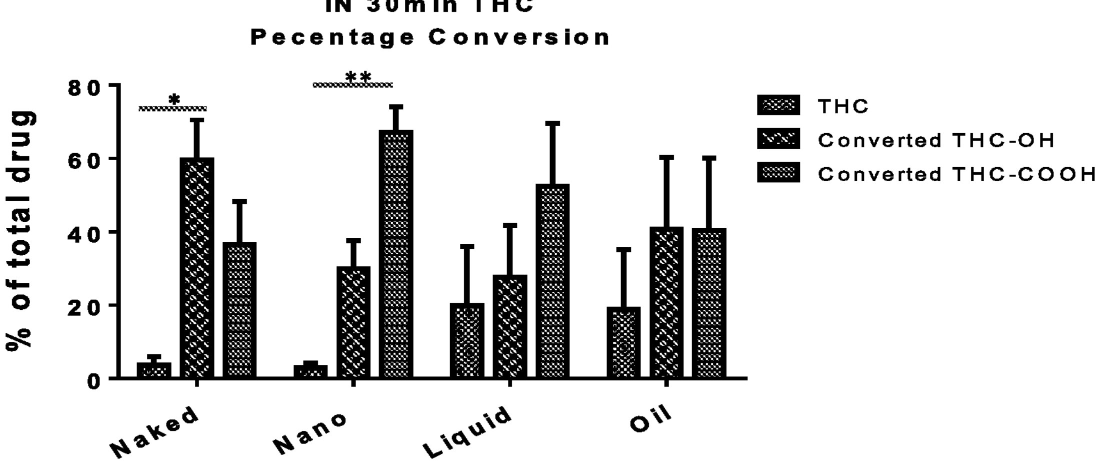
FIG. 7 shows percentage of total $\Delta^9$-THC administered converted to its metabolites for each indicated formulation 30 min after intranasal delivery.

The naked $\Delta^9$-THC formulation had a significant conversion of $\Delta^9$-THC to THC-OH ($p<0.05$), see FIG. 7. The nano-emulsion formulation treatment showed a significant conversion of $\Delta^9$-THC to THC-COOH after 30 minutes. This was an observed disadvantage associated with the nano-emulsion formulation.

Measurements Taken 45 Minutes after Formula Administration

Figure 8A:
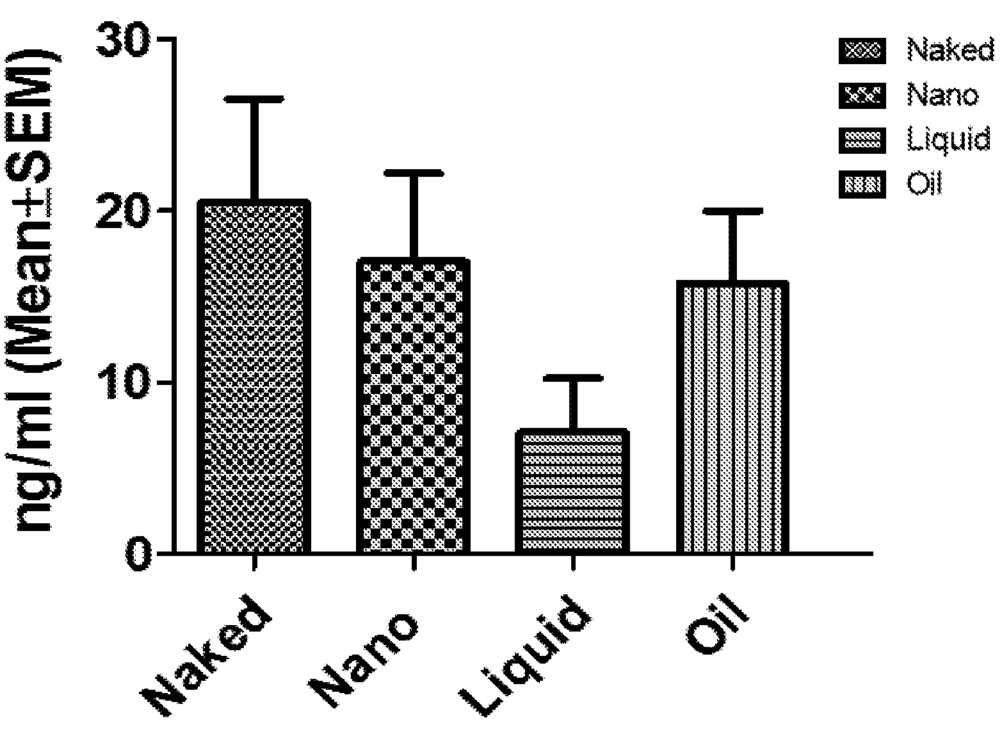
FIGS. 8A-8B show total drug ($\Delta^9$-THC and its metabolites) levels in blood and brain tissues for each indicated formulation 45 min after intranasal delivery.
Figure 8B:
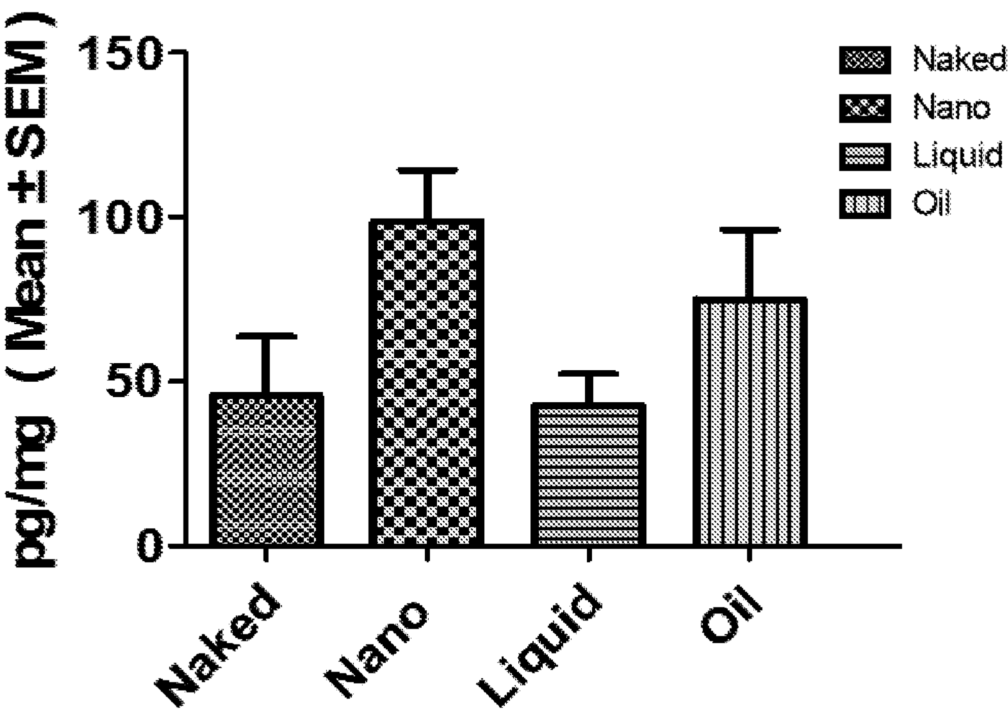
Figure 8C:
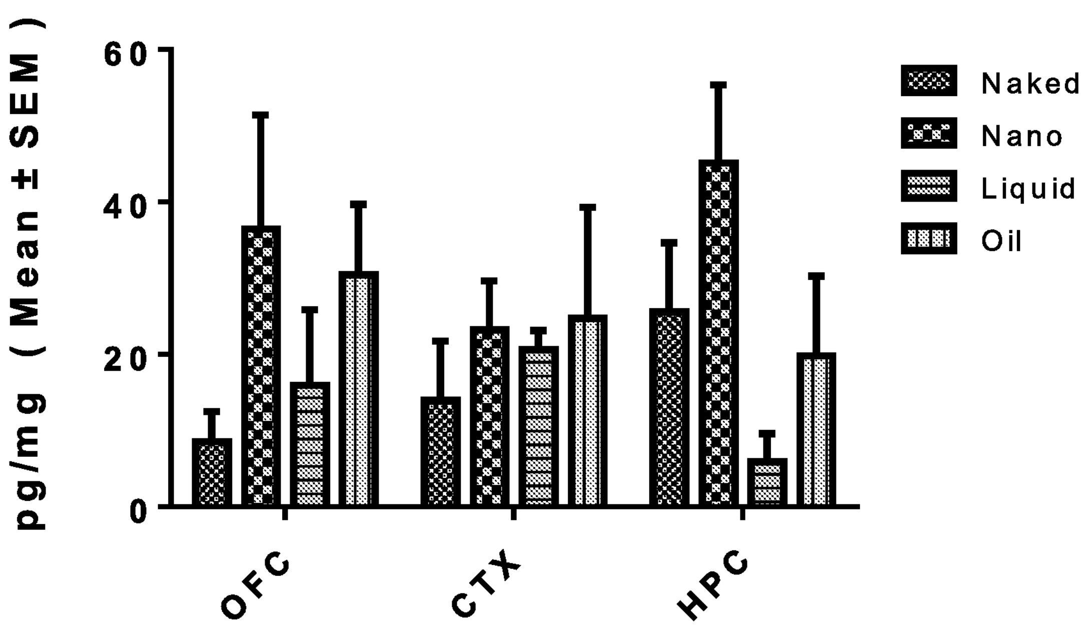
FIG. 8C provides a bar graph showing the distribution of total drug to different tissues of the brain.

All $\Delta^9$-THC formulation treatments showed detectable total drug levels 45 min after intranasal administration, see FIGS. 8A-8B. There was no significant difference in measured total drug levels between the formulations ($n=6$, $p<0.05$), see FIGS. 8A-8B.

Figure 9A:
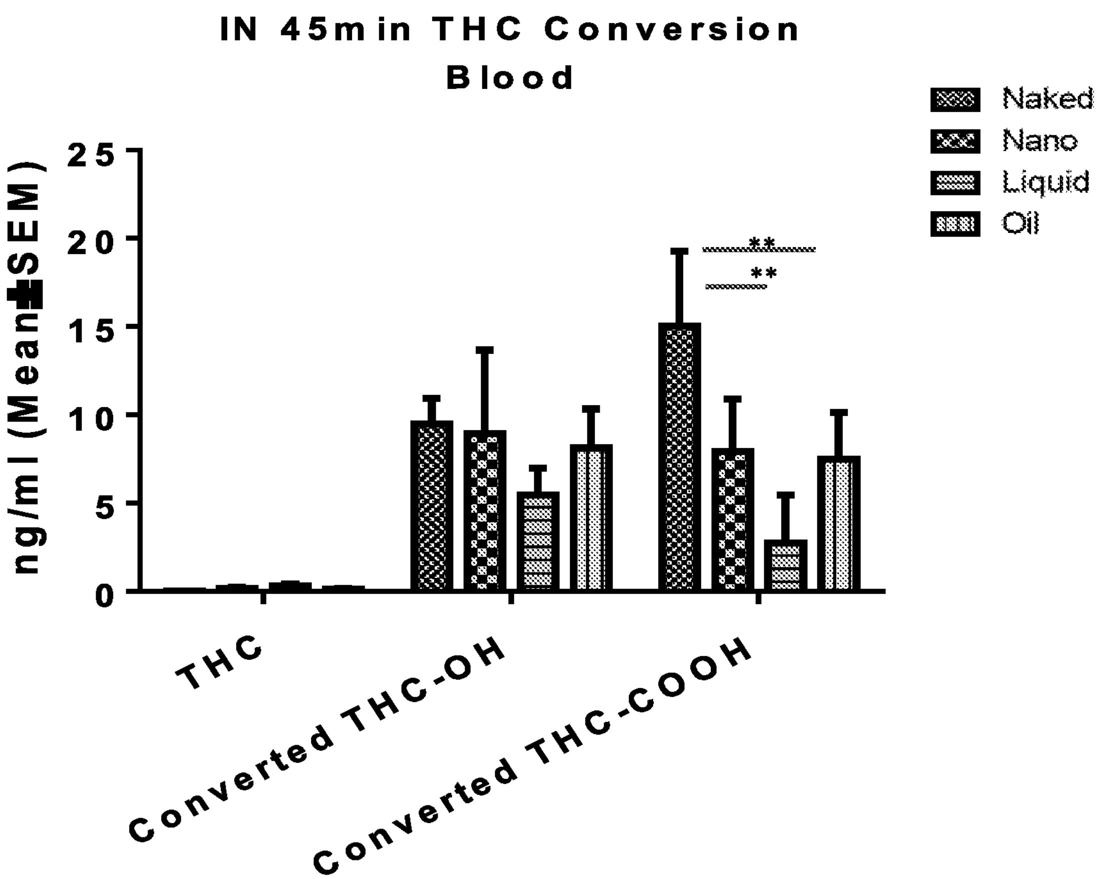
FIGS. 9A and 9B show conversion of $\Delta^9$-THC to its metabolites for each indicated formulation in blood and brain 45 min after intranasal delivery.
Figure 9B:
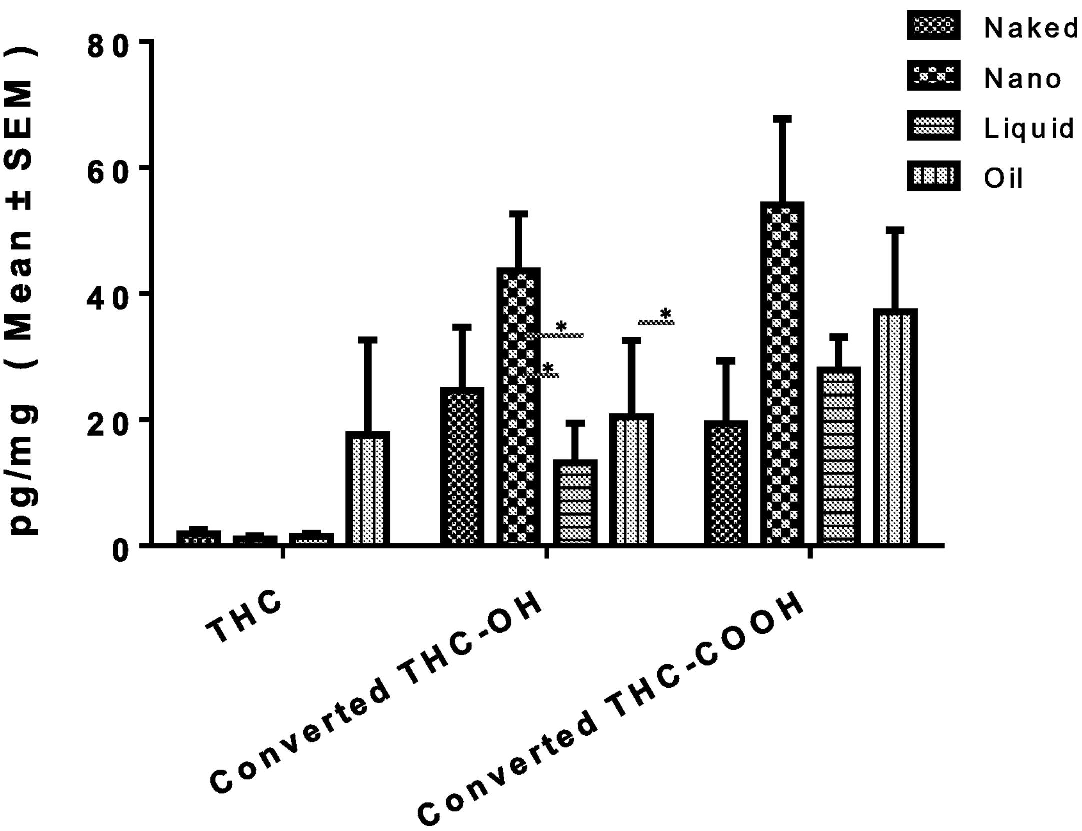

The naked $\Delta^9$-THC formulation treatment had a significantly higher conversion to COOH-THC compared to liquid and polymer-encapsulated $\Delta^9$-THC ($n=6$, $p<0.01$), see FIG. 9A. The animals treated with the nano-emulsion formulation had a higher conversion of $\Delta^9$-THC to THC-OH in brain tissues compared to the animals treated with the other formulations ($n=6$, $p<0.05$), see FIG. 9B. The treatment with the nano-emulsion formulation resulted in a significantly higher conversion of $\Delta^9$-THC to THC-COOH compared with the naked treatment in brain tissues as well ($n=6$, $p<0.05$), see FIG. 9B.

Figure 10:
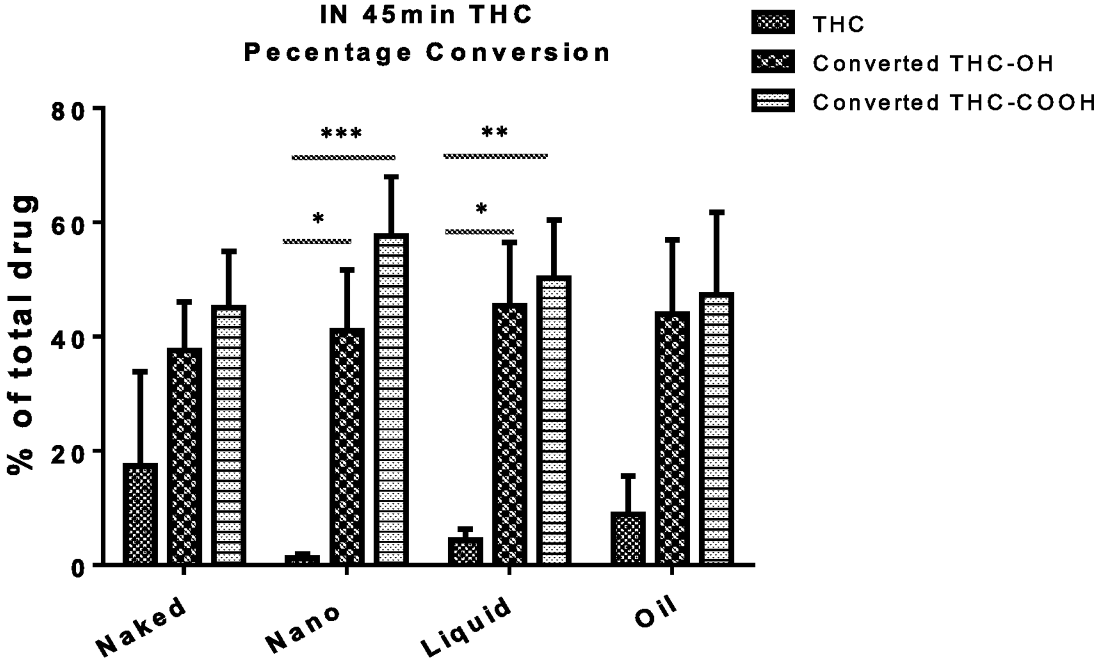
FIG. 10 provides a bar graph showing percentage of total $\Delta^9$-THC administered intranasally converted to its metabolites for each indicated formulation after 45 minutes.

The nano treatment resulted in significant conversion of $\Delta^9$-THC to both THC-OH and THC-COOH ($n=6$, $p<0.05$ and $p<0.001$, respectively), see FIG. 10. The liquid treatment also resulted in significant conversion of $\Delta^9$-THC to both THC-OH and THC-COOH ($n=6$, $p<0.05$ and $p<0.01$ respectively), see FIG. 10.

Measurements Taken 2 Hours after Formula Administration

Figure 11A:
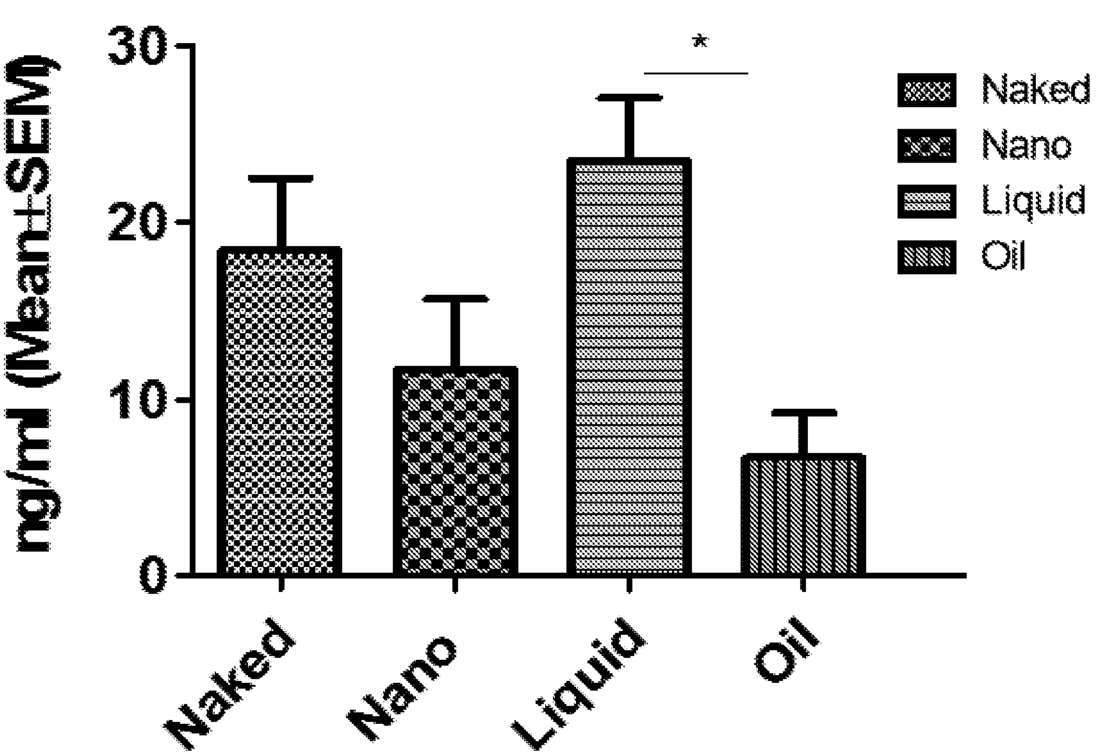
FIGS. 11A-11C show total drug ($\Delta^9$-THC and its metabolites) levels in blood and brain tissues for each indicated formulation 2 hours after intranasal delivery.
Figure 11B:
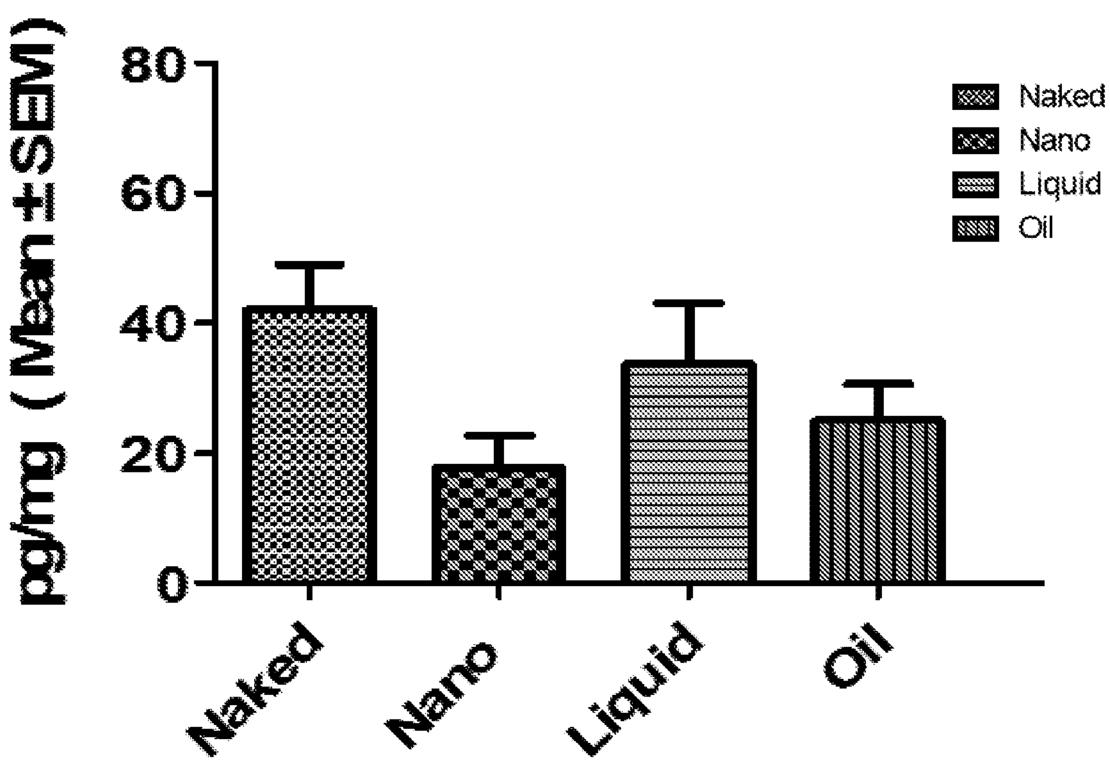
Figure 11C:
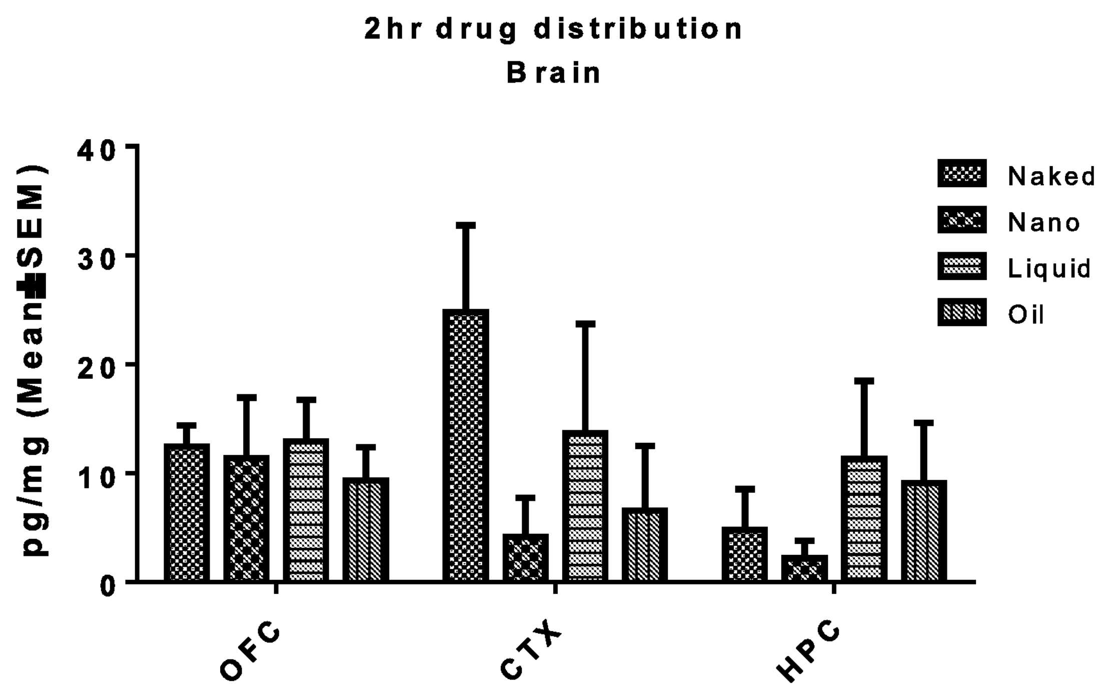

All treatments resulted in detectable total drug levels 2 hours after intranasal administration, see FIG. 11A-11C. There was a significant difference in measured total drug levels in blood between the liquid and oil treatments with liquid resulting in higher total drug after 2 hours ($n=6$, $p<0.05$), see FIG. 11A.

Figure 12A:
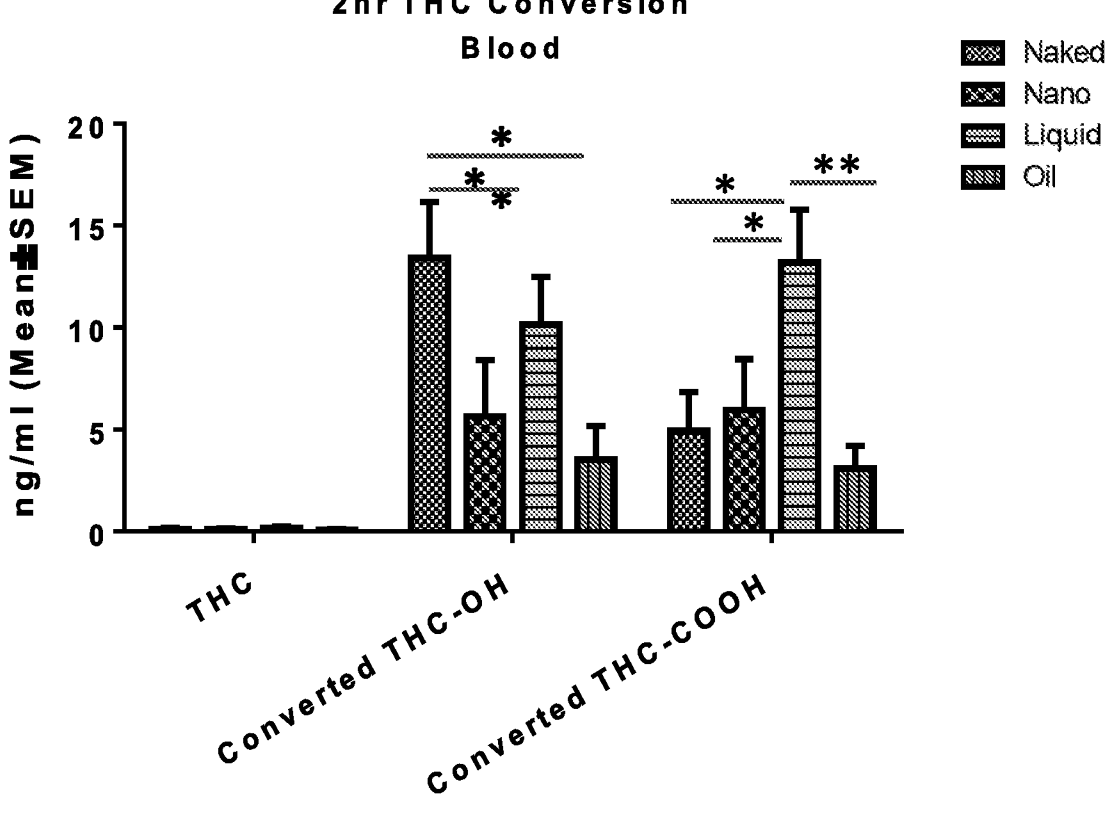
FIGS. 12A and 12B show conversion of $\Delta^9$-THC to its metabolites OH-THC and COOH-THC for each indicated formulation 2 hours after intranasal delivery.
Figure 12B:
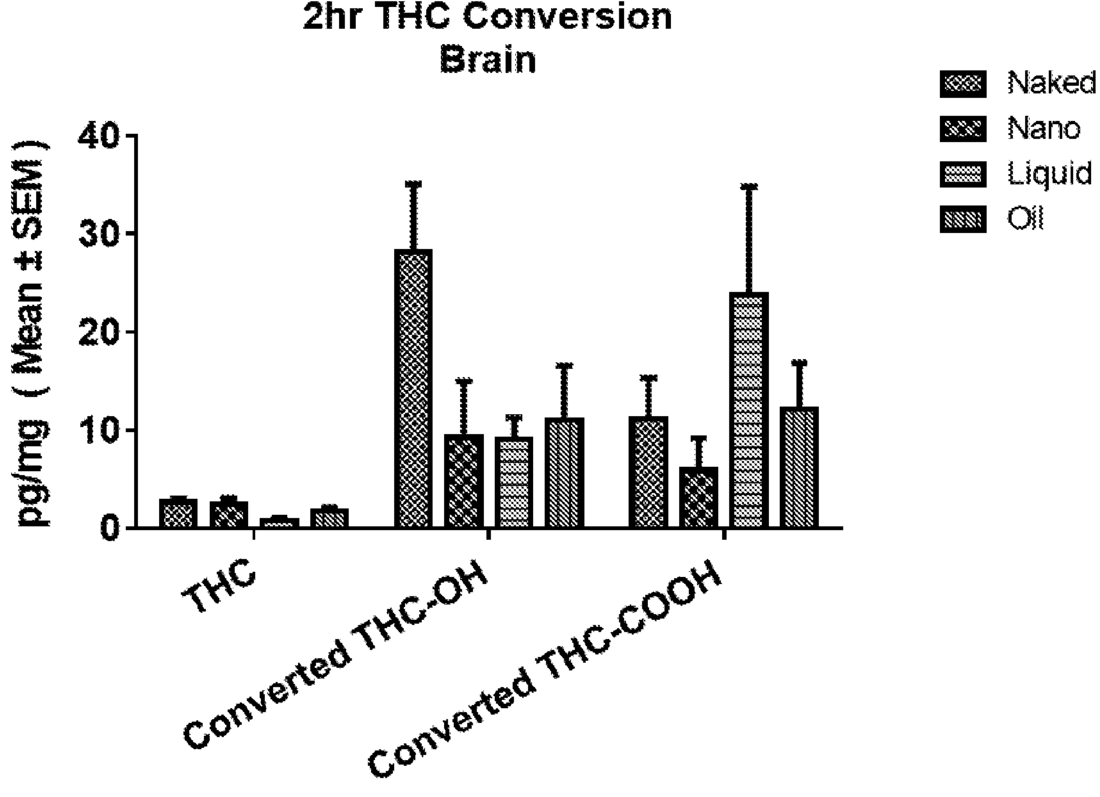

In whole blood, the oil formulation treatment resulted in a significantly higher conversion to THC-COOH than all other formulations, see FIG. 12A. This was an observed disadvantage of the oil formulation. The naked formulation treatment resulted in a significantly higher conversion to THC-OH after 2 hours compared with the nano and liquid formulations. ($n=6$, $p<0.05$), see FIG. 12B.

Figure 13:
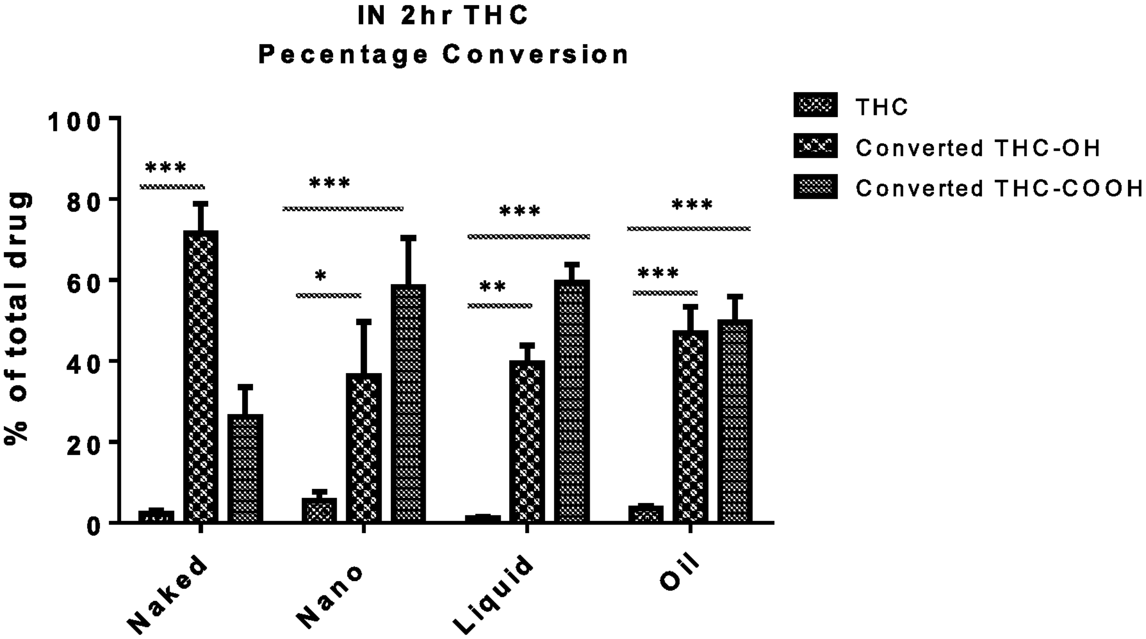
FIG. 13 provides a bar graph showing percentage of total $\Delta^9$-THC administered intranasally converted to its metabolites for each indicated formulation after 2 hours.
Figure 14A:
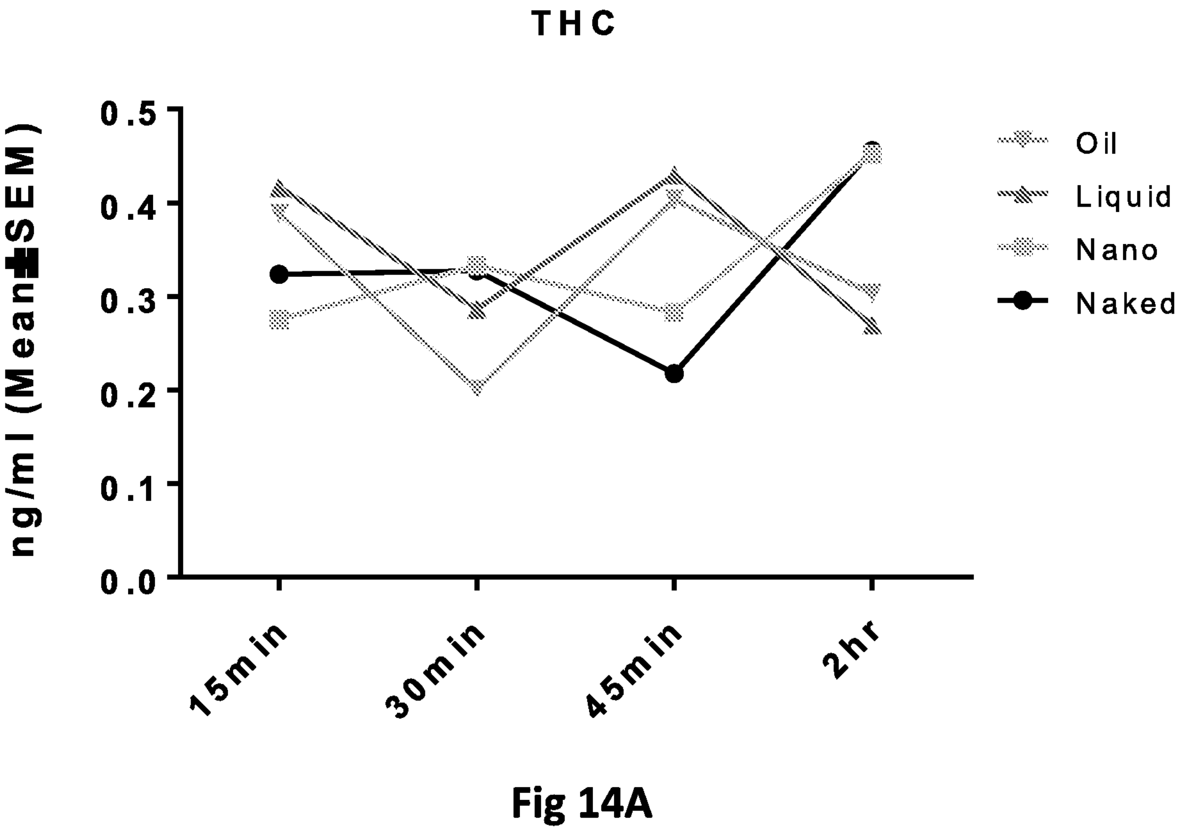
FIGS. 14A-14D show detection of $\Delta^9$-THC and its metabolites for each indicated formulation over time following intranasal delivery.
Figure 14B:
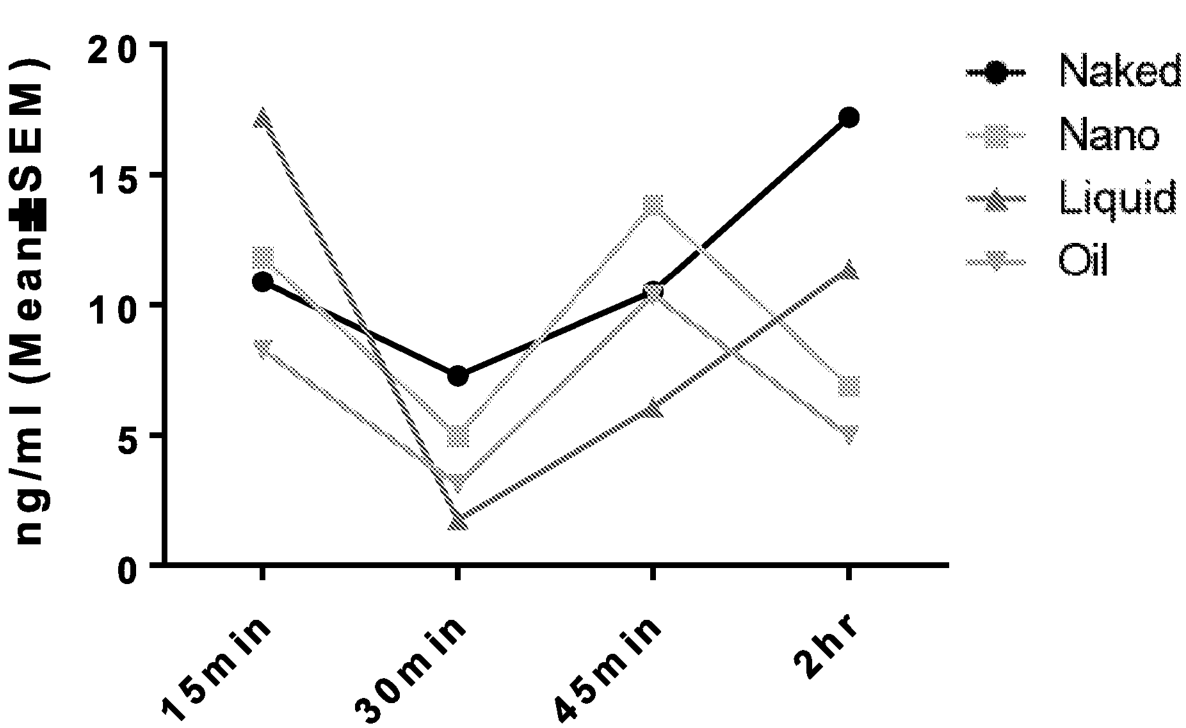
Figure 14C:
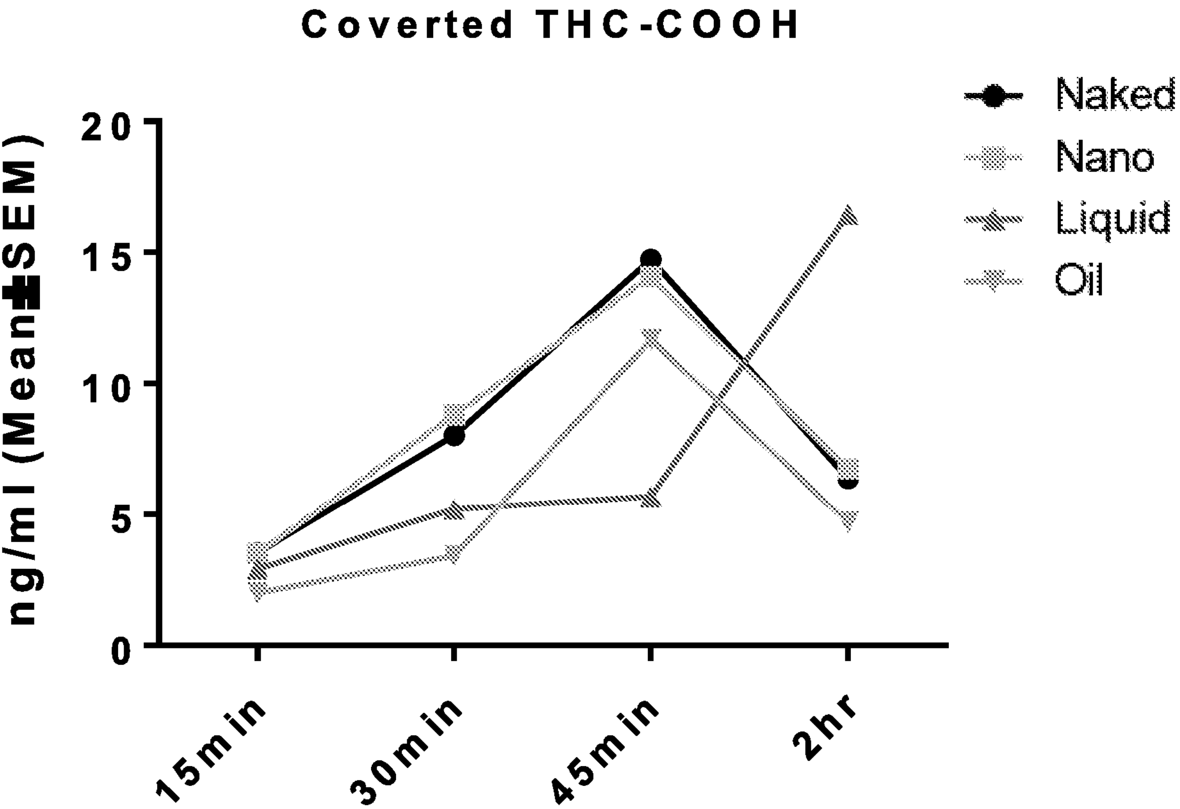
Figure 14D:
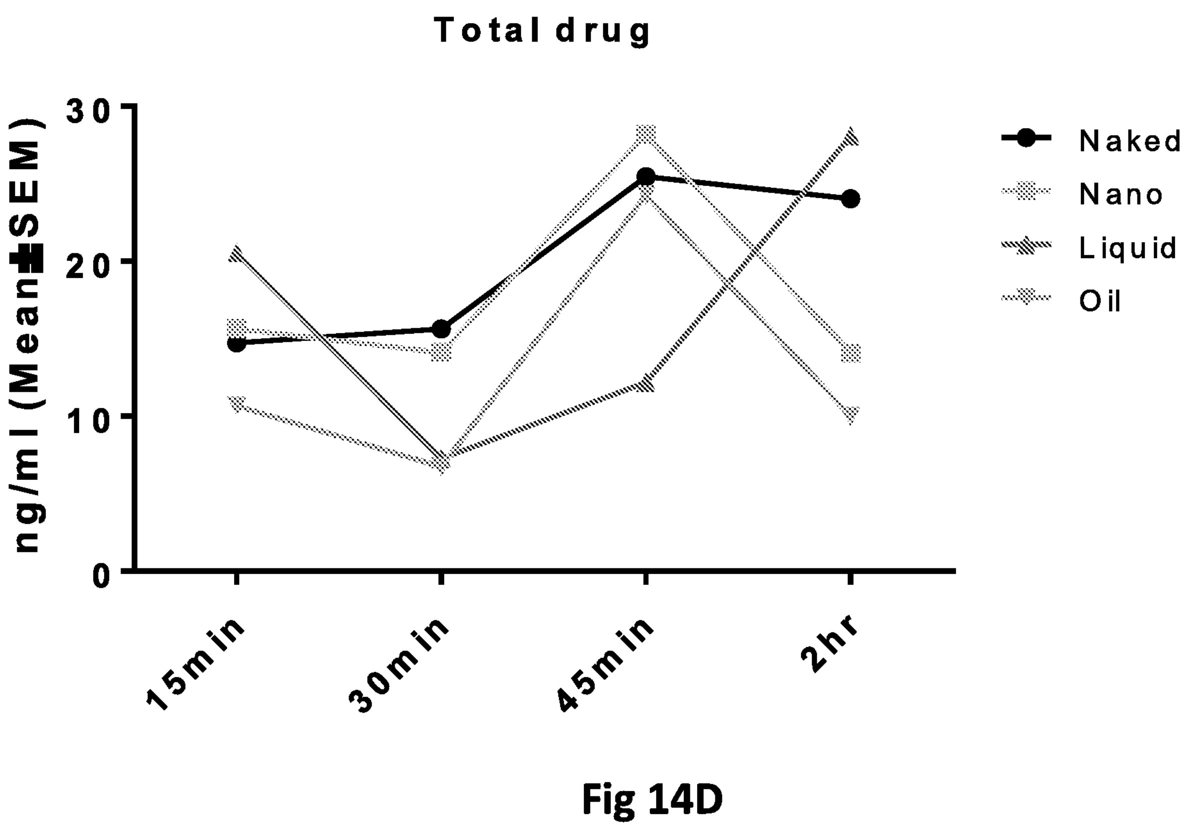

Naked formulation treatments resulted in significant conversion of $\Delta^9$-THC to OH-THC ($n=6$, $p<0.001$), see FIG. 13. The nano, liquid, and oil formulation treatments resulted in $\Delta^9$-THC being significantly converted to both THC-OH and THC-COOH. The oil formulation treatment resulted in the least conversion of $\Delta^9$-THC to THC-OH after 2 hours, see FIGS. 14A and 14B.

Example 7. Administration of Polymeric Micelle Encapsulated $\Delta^9$-THC to Mice An experiment was conducted to compare the distribution of $\Delta^9$-THC and $\Delta^9$-THC metabolites in mice following administration of (alternatively, "treatment with") the polymeric micelle encapsulated $\Delta^9$-THC formulation (polymer-THC) and the naked $\Delta^9$-THC formulation (naked THC). Following administration of each formula, mice were sacrificed after 30 min. Blood samples (350 μl) were collected by intracardial punctuation, and brains were removed and dissected into different regions (olfactory (OFC), front cortex, back cortex (collectively CTX), and hippocampus (HPC)). Each brain tissue sample was 5.0-6.0 mg. The mice administered the formulations were 5-month old mice of mixed background (mix of strains C57B6, SJL, and B6D2F1) were used.

Four mice were administered each of the two formulations (n=4 for each formulation), and one control group of mice (n=4) was not administered either of the two formulations. The formulations were each delivered by intranasal delivery.

Figure 16A:
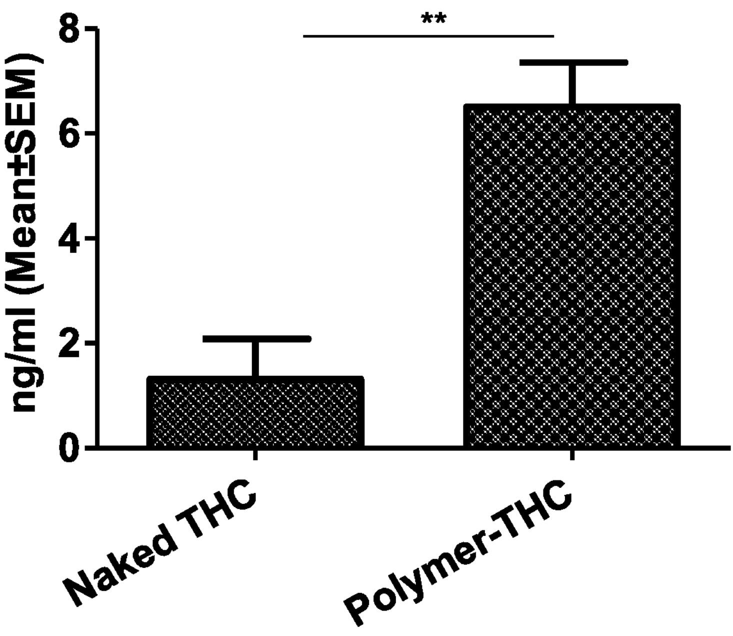
FIGS. 16A-16C show total drug ($\Delta^9$-THC and its metabolites) levels and conversion in blood and brain tissues for each indicated formulation 30 min after intranasal delivery and drug distribution within the brain.
Figure 16B:
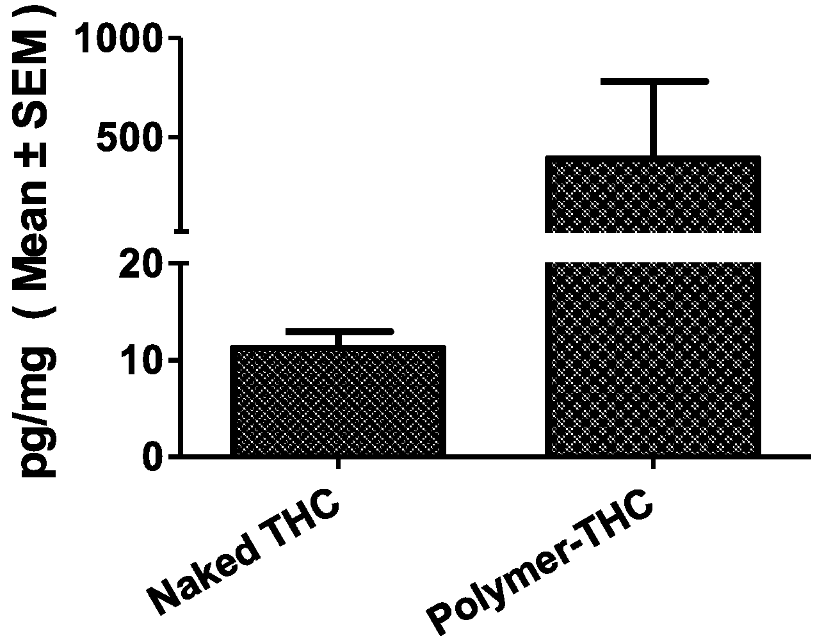

The polymer-THC treatment resulted in significantly higher measured total drug in blood after 30 minutes than the treatment with the naked THC formulation ($p<0.01$), see FIG. 16A. The polymer-THC treatment also resulted in significantly higher levels of $\Delta^9$-THC in blood than the naked THC treatment ($p<0.001$), see FIG. 16A, and higher levels of $\Delta^9$-THC in brain than the naked THC treatment, see FIG. 16B. Also, the polymer $\Delta^9$-THC treatment resulted in lower levels of conversion of $\Delta^9$-THC to OH-THC and COOH-THC than the naked THC treatment in blood and brain after 30 min, see FIGS. 16A and 16B.

After 30 minutes, both treatments resulted in very little $\Delta^9$-THC being converted to THC-COOH ($p<0.05$), and there was measured conversion to OH-THC. The polymer-THC treatment resulted in significantly more $\Delta^9$-THC as a percentage of total drug than OH-THC or COOH-THC after 30 minutes ($p<0.01$). Compared with the naked THC treatment, the polymer $\Delta^9$-THC treatment resulted in less conversion of $\Delta^9$-THC to OH-THC or COOH-THC.

Examples 2 and 7 demonstrate the successful generation of stable copolymeric micelles encapsulating $\Delta^9$-THC, using certain hydrophilic and hydrophobic polymers to form a water-soluble carrier for the cannabinoid (Example 2) and successful administration of the stable polymeric micelles encapsulating $\Delta^9$-THC to a mammal (Example 7). The polymeric micelles encapsulating $\Delta^9$-THC were successfully delivered to the brain. The polymeric micelles facilitated drug delivery and increase drug availability in the brain. $\Delta^9$-THC can often be hard to handle and is a sticky substance, which can lead to difficulties in drug administration and dose measurement. Therefore, the water-soluble stable polymeric micelles encapsulating $\Delta^9$-THC are a more easily handleable alternative to naked THC for drug delivery. Encapsulation of $\Delta^9$-THC in a polymeric micelle allows $\Delta^9$-THC to become soluble in water and delivered in a more consistent manner to a patient relative to naked THC. In view of Examples 6 and 7, the polymeric micelle encapsulating $\Delta^9$-THC formulations achieved the best balance of few components, ease and simplicity of manufacture, and clinically-relevant results (e.g., metabolite control and rate of delivery) in comparison to the other formulations evaluated.

Figure 15A:
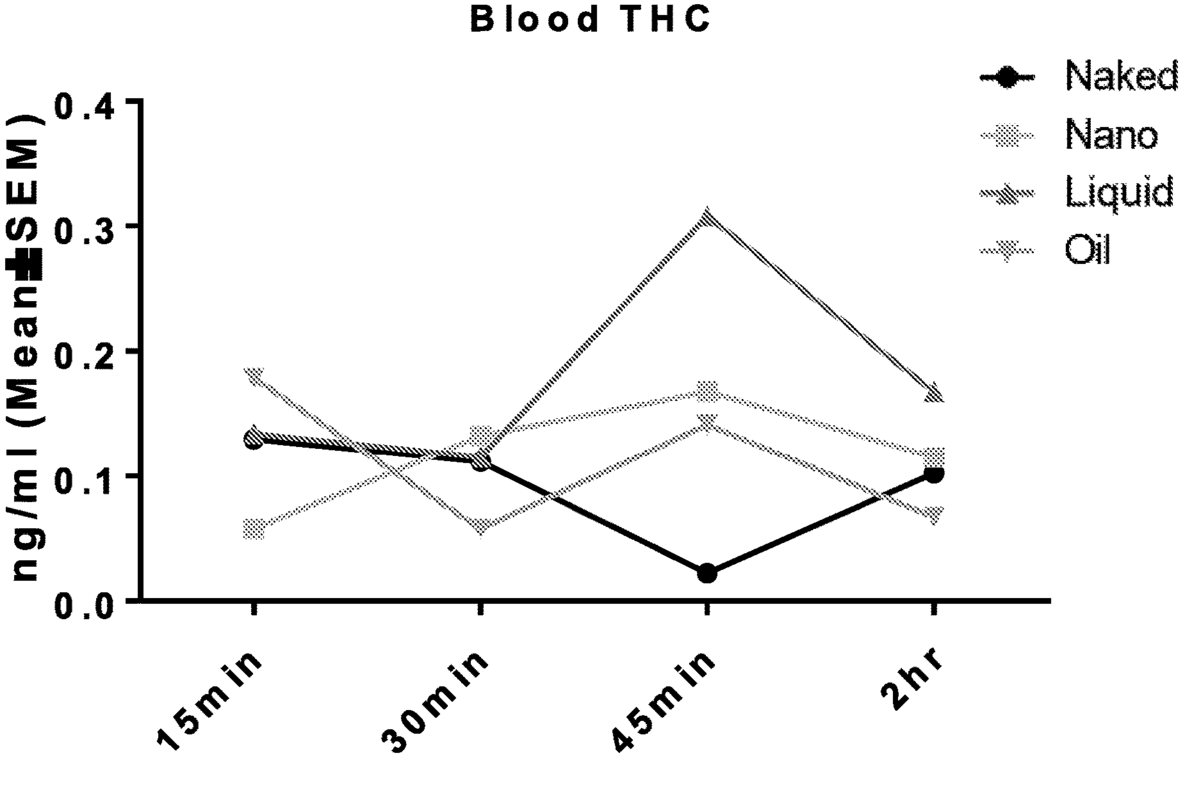
FIGS. 15A-15F show detection of $\Delta^9$-THC and its metabolites in blood and brain for each indicated formulation over time following intranasal delivery.
Figure 15B:
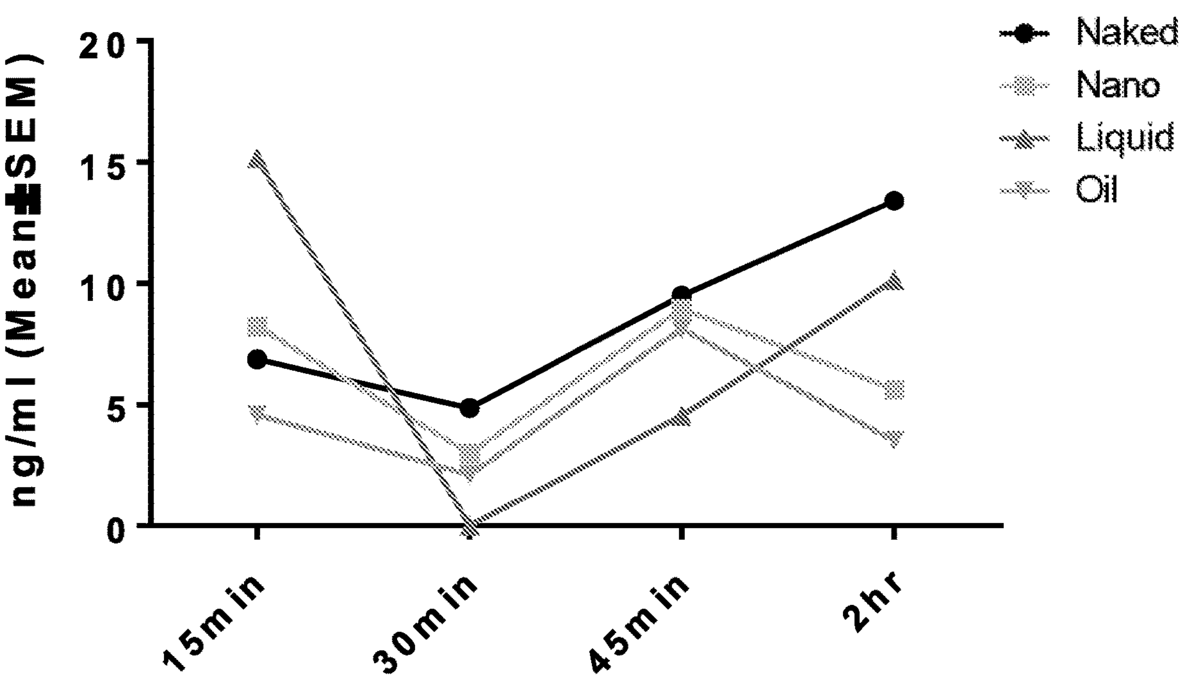
Figure 15C:
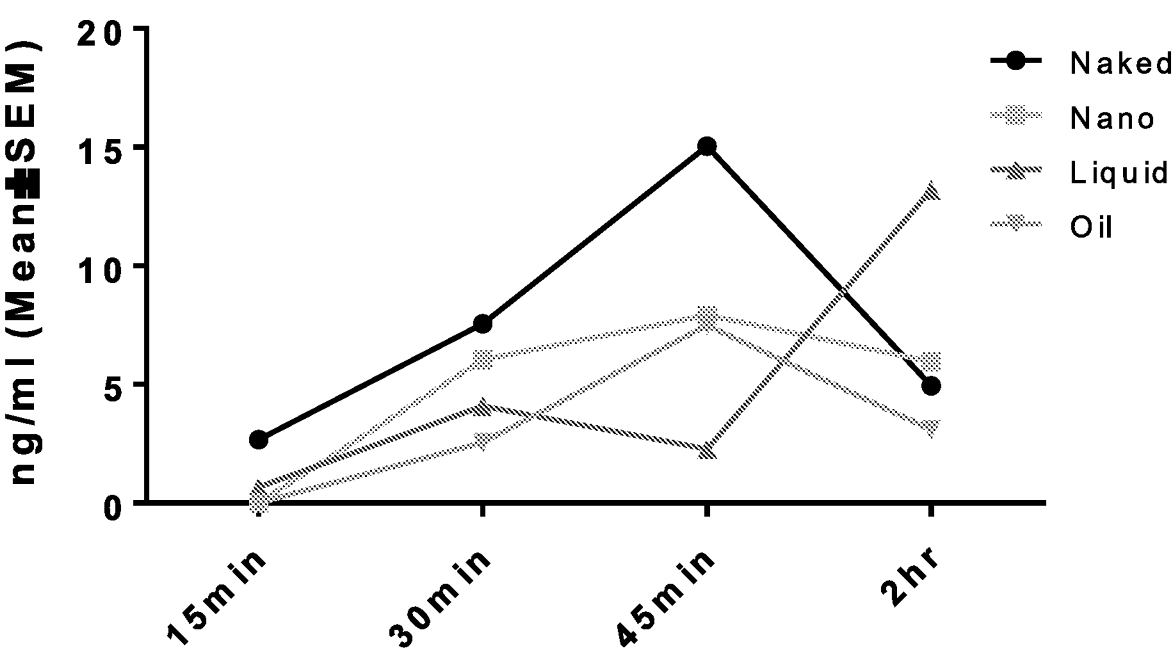
Figure 15D:
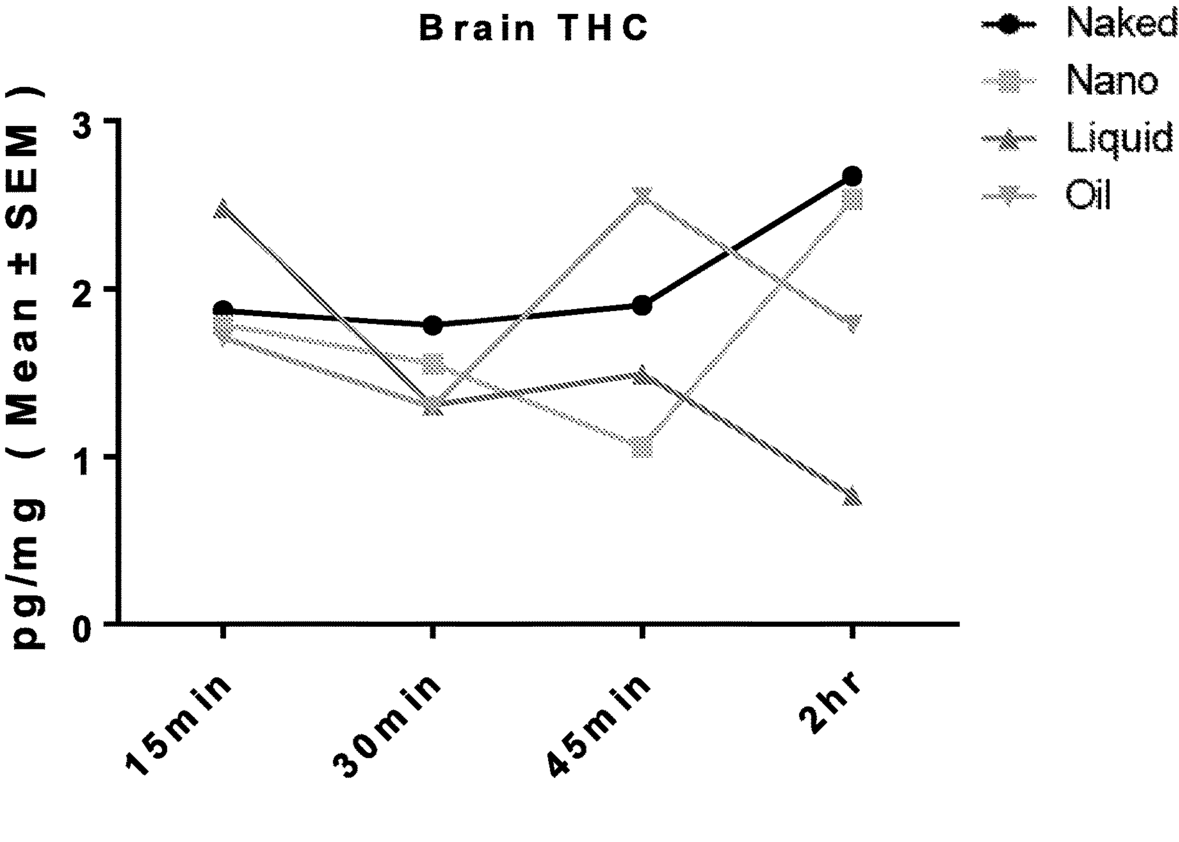
Figure 15E:
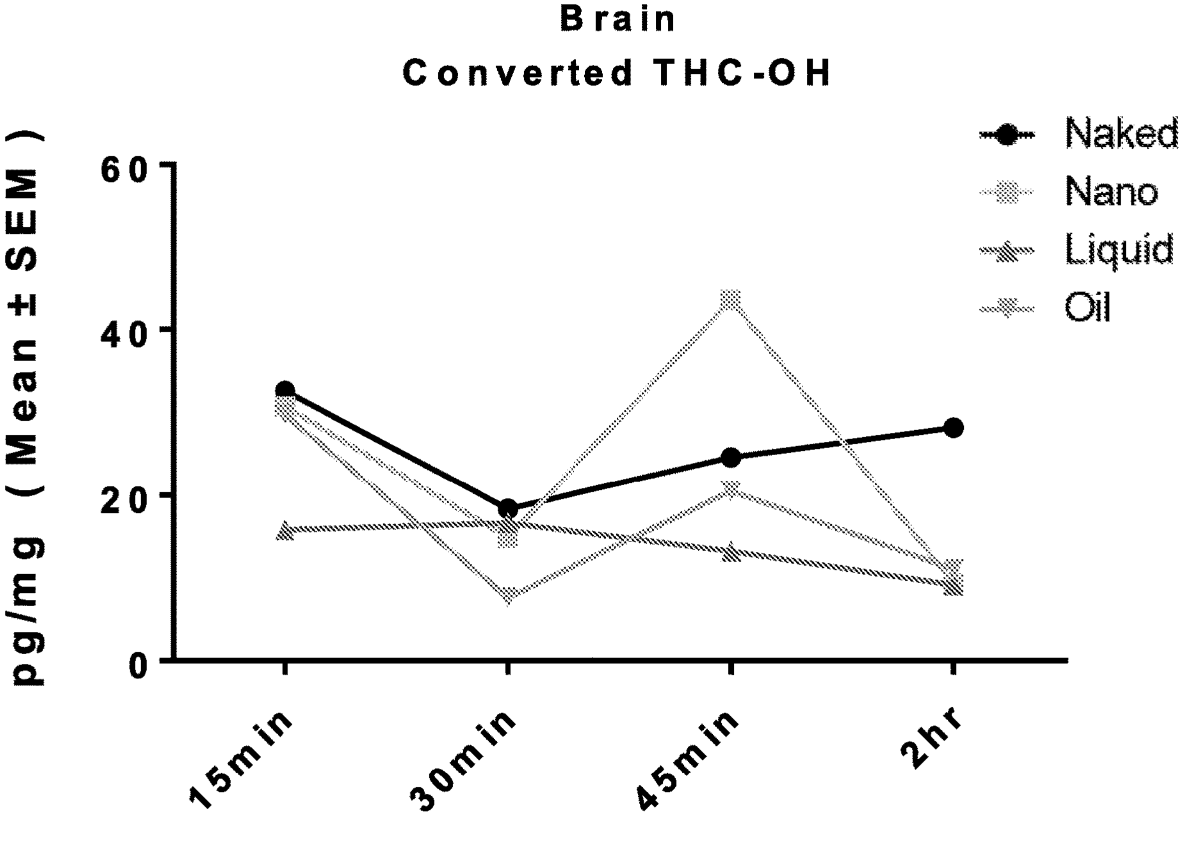
Figure 15F:
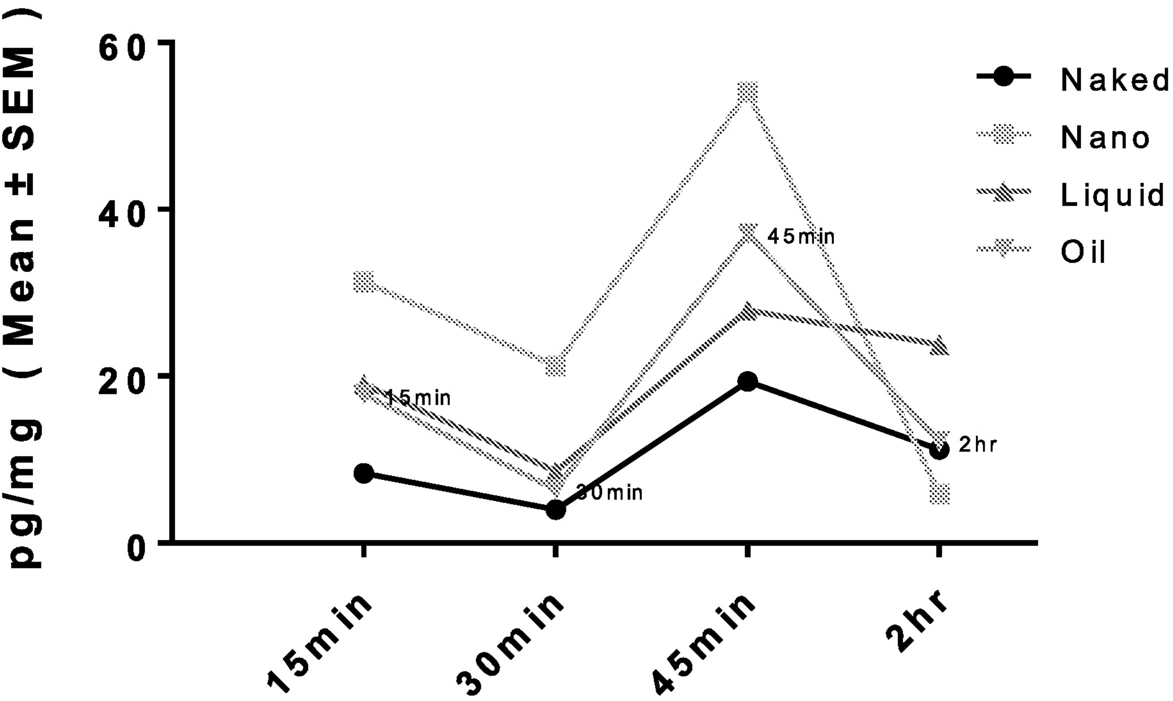
Figure 16C:
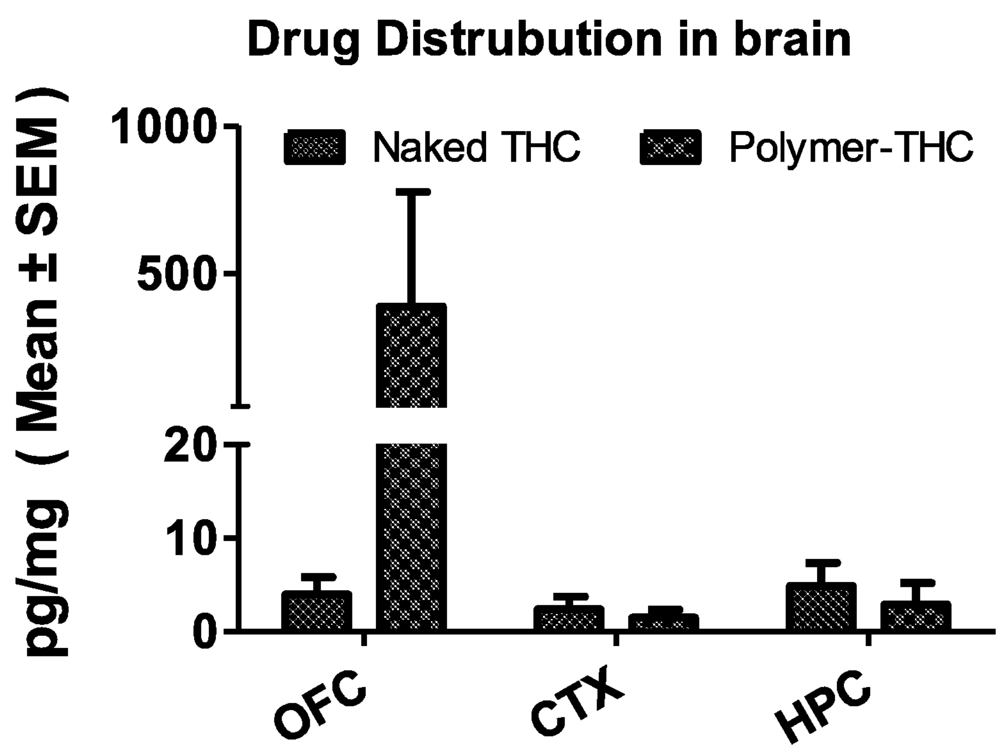
Figure 17A:
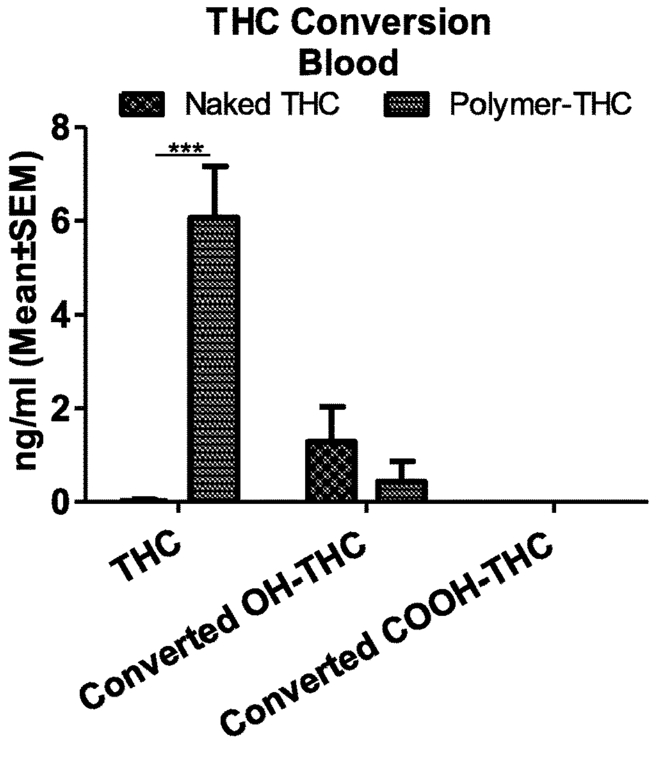
FIGS. 17A and 17B show conversion of $\Delta^9$-THC in blood and brain tissues for each indicated formulation 30 min after intranasal delivery.
Figure 17B:
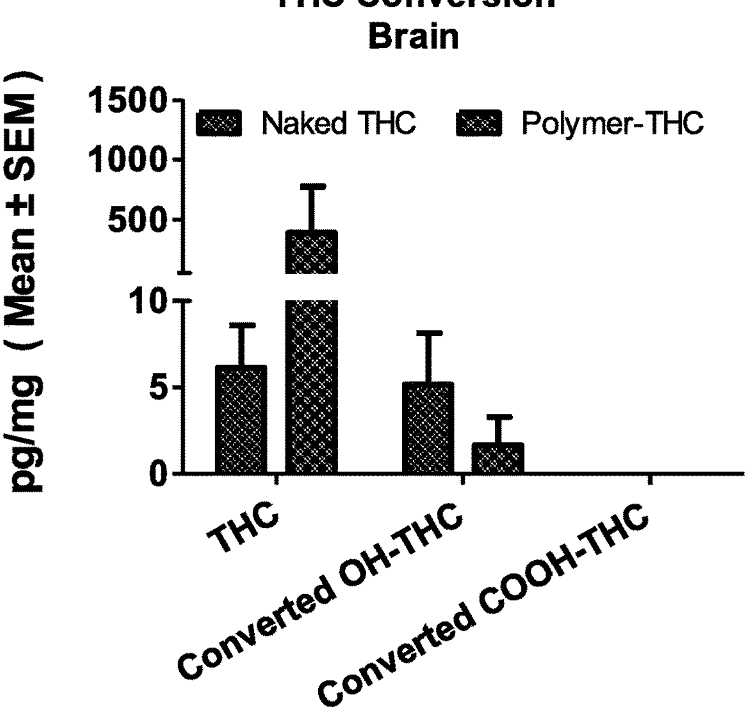
Figure 18:
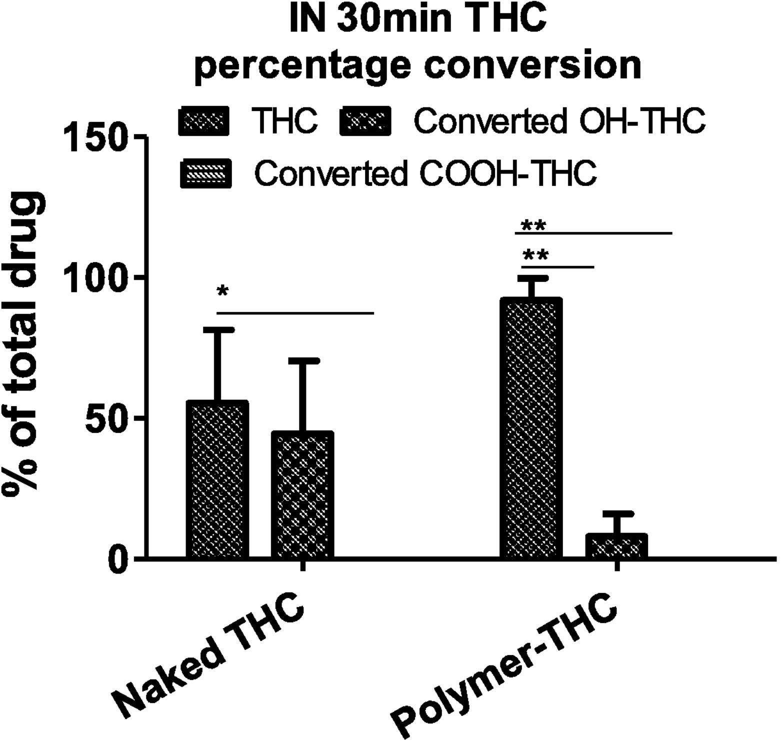
FIG. 18 provides a bar graph showing percentage of total drug administered intranasally converted to its metabolites for each indicated formulation after 30 minutes.

The polymeric micelle encapsulated $\Delta^9$-THC formulation (Example 2) showed superior performance in several respects. First, the poly formulation resulted in higher $\Delta^9$-THC metabolic stability relative to naked $\Delta^9$-THC at 30 minutes, as demonstrated by a slower conversion of $\Delta^9$-THC to its metabolites (FIGS. 16-17). See also, FIGS. 5-6. Second, the poly formulation resulted in more efficient delivery of $\Delta^9$-THC to blood and brain relative to naked $\Delta^9$-THC (FIG. 15A). See also, FIG. 4A-4B. Third, the poly formulation showed selective delivery of $\Delta^9$-THC to the olfactory cortex and/or the hippocampus brain regions, whereas naked THC shows either no selective drug delivery to any brain region or some preferential delivery to the frontal cortex. See, FIGS. 15C and 4C.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. It is further to be understood that all values are approximate and are provided for description.

Recitation of ranges of values herein are merely intended to serve as a shorthand method of referring individually to each separate value falling within the range and each endpoint, unless otherwise indicated herein, and each separate value and endpoint is incorporated into the specification as if it were individually recited herein.

Patents, patent applications, publications, product descriptions, and protocols are cited throughout this application, the disclosures of which are incorporated herein by reference in their entireties for all purposes.

The invention claimed is:

1. A method of treating a neurological condition in a patient identified as in need thereof comprising the step of:

administering to the patient, intranasally or through inhalation, formulated to target the brain of the patient a pharmaceutical composition comprising (i) a therapeutically effective amount of a cannabinoid selected from $\Delta^9$-THC and cannabinodiol (CBD), or a pharmaceutically acceptable salt or solvate thereof; and (ii) an amphiphilic copolymer comprising at least one hydrophilic component comprising polyethylene glycol (PEG) and at least one hydrophobic component selected from polycaprolactone (PCL), polylactic acid (PLA), poly lactide co-glycolide (PLGA), and a combination thereof;

wherein the ratio of the cannabinoid to the amphiphilic copolymer is greater than 1:10 by weight, and said cannabinoid is encapsulated in said amphiphilic copolymer, and wherein said neurological condition is selected from Alzheimer's disease, Parkinson's disease, neuropathic pain, spasticity, spinal-cord-injury-induced pain, migraines, multiple sclerosis, Tourette Syndrome, and post-traumatic stress disease (PTSD).

2. The method of claim 1, wherein said hydrophilic and hydrophobic components are in a ratio, by number average molecular weight, of about 1:1 to 1:5.

3. The method of claim 1, wherein said hydrophilic component is polyethylene glycol (PEG) having a number average molecular weight of about 2000 and said hydrophobic component is poly lactide co-glycolide (PLGA) having a molecular weight of about 4500.

4. The method of claim 1, wherein said therapeutically effective amount of cannabinoid is about 0.2 to 7.5 mg.

5. The method of claim 1, wherein said pharmaceutical composition is administered once daily or twice daily.

* * * * *